(12) United States Patent
Elias et al.

(10) Patent No.: US 9,102,744 B2
(45) Date of Patent: Aug. 11, 2015

(54) CONJUGATED ANTI-CD38 ANTIBODIES

(75) Inventors: Kathleen Ann Elias, San Francisco, CA (US); Gregory Landes, San Bruno, CA (US); Shweta Singh, South San Francisco, CA (US); Wouter Korver, South San Francisco, CA (US); Andrew Walling Drake, South San Francisco, CA (US); Mary Haak-Frendscho, San Francisco, CA (US); Gyorgy Pal Snell, San Francisco, CA (US); Vinay Bhaskar, South San Francisco, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 14 days.

(21) Appl. No.: 13/977,207

(22) PCT Filed: Dec. 30, 2011

(86) PCT No.: PCT/US2011/068244
§ 371 (c)(1),
(2), (4) Date: Feb. 13, 2014

(87) PCT Pub. No.: WO2012/092616
PCT Pub. Date: Jul. 5, 2012

(65) Prior Publication Data
US 2014/0155584 A1 Jun. 5, 2014

Related U.S. Application Data

(60) Provisional application No. 61/485,104, filed on May 11, 2011, provisional application No. 61/470,406, filed on Mar. 31, 2011, provisional application No. 61/470,382, filed on Mar. 31, 2011, provisional application No. 61/428,699, filed on Dec. 30, 2011.

(51) Int. Cl.
| | |
|---|---|
| C07K 16/00 | (2006.01) |
| C07K 16/40 | (2006.01) |
| C07K 16/28 | (2006.01) |
| C12N 9/99 | (2006.01) |
| A61K 39/00 | (2006.01) |

(52) U.S. Cl.
CPC ............ *C07K 16/40* (2013.01); *C07K 16/2896* (2013.01); *C12N 9/99* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,829,673 B2 | 11/2010 | De Weers et al. |
| 8,088,896 B2 | 1/2012 | Tesar et al. |
| 2009/0076249 A1 | 3/2009 | De Weers et al. |
| 2009/0148449 A1 | 6/2009 | De Weers et al. |
| 2011/0099647 A1 | 4/2011 | De Weers et al. |
| 2011/0262454 A1 | 10/2011 | Park et al. |

FOREIGN PATENT DOCUMENTS

| | | |
|---|---|---|
| WO | WO2006/099875 | 9/2006 |
| WO | WO2006/125640 | 11/2006 |

OTHER PUBLICATIONS

De Weers et. al., "Daratumumab, a Novel Therapeutic Human CD38 Monoclonal Antibody, Induces Killing of Multiple Myeloma and Other Hematological Tumors", J Immunology, 2010, 186(3): 1840-1848.
Ellis et al., "Engineered Anti-CD38 Monoclonal Antibodies for Immunotherapy of Multiple Myeloma", J Immunology, 1995, 155: 925-9237.
Goldmacher et al., Anti-CD38-blocked-ricin; An immunotoxin for the treatment of multiple myeloma, Blood vol. 84 p. 3017 (1994).
Groen, Richard W. et al., "In Vitro and In Vivo Efficacy of CD38 Directed Therapy with Daratumumab in the Treatment of Multiple Myeloma", Blood, vol. 116, No. 21, Nov. 2010, pp. 1261-1262, XP009157537.
Kong, Sun-Young et al., "Daratumumab Directly Induces Human Multiple Myeloma Cell Death and Acts Synergistically with Conventional and Novel Anti-Myeloma Drugs", Blood, vol. 116, No. 21, Nov. 2010, pp. 1241-1242, XP009157536.
Little, M. et. al., "Of mice and men: hybridoma and recombinant antibodies", Immunology Today, El Sevier Publications, Cambridge, GB, vol. 21, No. 8, Aug. 2000, pp. 364-370, XP004215163.
Odendahl M., "Disturbed peripheral B lymphocyte homeostasis in systemic lupus erythematosus.", J Immunol. Nov. 15, 2000;165(10):5970-9.
Odendahl M., "Perturbations of peripheral B lymphocyte homoeostasis in children with systemic lupus erythematosus.", Ann Rheum Dis. Sep. 2003;62(9):851-8.
Owczarczyk K., "A plasmablast biomarker for nonresponse to antibody therapy to CD20 in rheumatoid arthritis.", Sci Transl Med. Sep. 21, 2011;3(101):101ra92.
Park, Peter U. et al., "SAR650984: A Potent Anti-CD38 Therapeutic Antibody with Three Mechanisms of Action (Apoptosis, ADCC, CDC) for Hematological Malignancies.", Blood, vol. 112, No. 11, Nov. 2008, p. 951, XP009157535.
Pavon E.J., "Increased association of CD38 with lipid rafts in T cells from patients with systemic lupus erythematosus and in activated normal T cells.", Mol Immunol. Mar. 2006;43(7):1029-39. Epub Jun. 16, 2005.
Stevenson et al., "Preliminary studies for an immunotherapeutic approach to the treatment of human myeloma using chimeric anti-CD38 antibody", Blood, 1991, 77: 1071-1079.
Vital E.M., "Management of nonresponse to rituximab in rheumatoid arthritis: predictors and outcome of re-treatment.", Arthritis Rheum. May 2010;62(5):1273-9.
International Search Report and Written Opinion of the International Searching Authority dated Mar. 28, 2012 for PCT/US11/68244.
International Search Report and Written Opinion of the International Searching Authority dated May 2, 2012 for PCT/US11/68235.

Primary Examiner — Sheela J Huff
(74) Attorney, Agent, or Firm — Robin M. Silva; Christina A. MacDougall; Morgan, Lewis & Bockius, LLP

(57) ABSTRACT

Isolated antibodies that bind to human CD38 and cynomolgus CD38 are disclosed. Also disclosed are pharmaceutical compositions comprising the disclosed antibodies, and therapeutic and diagnostic methods for using the disclosed antibodies.

17 Claims, 20 Drawing Sheets

FIGURE 2

Ab79 Heavy Chain (SEQ ID NO:21)

EVQLLESGGGLVQPGGSLRLSCAASGFTFDDYGMSWVRQAPGKGLEWVSDIS
WNGGKTHYVDSVKGQFTISRDNSKNTLYLQMNSLRAEDTAVYYCARGSLFH
DSSGFYFGHWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVD
KSRWQQGNVFSCSVMHEALHNHYTQKSLSLSPGK

Ab79 Light Chain (SEQ ID NO:22)

QSVLTQPPSASGTPGQRVTISCSGSSSNIGDNYVSWYQQLPGTAPKLLIYRDSQ
RPSGVPDRFSGSKSGTSASLAISGLRSEDEADYYCQSYDSSLSGSVFGGGTKLT
VLGQPKANPTVTLFPPSSEELQANKATLVCLISDFYPGAVTVAWKADGSPVK
AGVETTKPSKQSNNKYAASSYLSLTPEQWKSHRSYSCQVTHEGSTVEKTVAP
TECS

Ab19 Heavy Chain (SEQ ID NO:11)

EVQLLESGGGLVQPGGSLRLSCAASGFTFNNYDMTWVRQAPGKGLEWVAVI
SYDGSDKDYADSVKGRFTISRDNSKNTLYLQMNSLRAEDTAVYYCARVYYY
GFSGPSMDVWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVD
KSRWQQGNVFSCSVMHEALHNHYTQKSLSLSPGK

Ab19 Light Chain (SEQ ID NO:12)

QSVLTQPPSASGTPGQRVTISCSGSNSNIGSNTVNWYQQLPGTAPKLLIYSDSN
RPSGVPDRFSGSKSGTSASLAISGLRSEDEADYYCQSYDSSLSGSRVFGGGTKL
TVLGQPKANPTVTLFPPSSEELQANKATLVCLISDFYPGAVTVAWKADGSPV
KAGVETTKPSKQSNNKYAASSYLSLTPEQWKSHRSYSCQVTHEGSTVEKTVA
PTECS

FIGURE 3

**CD38 *Homo sapiens* (Accession NP_001766.2; SEQ ID NO:1)**

MANCEFSPVSGDKPCCRLSRRAQLCLGVSILVLILVVVLAVVVPRWRQQWSGPGTTKR
FPETVLARCVKYTEIHPEMRHVDCQSVWDAFKGAFISKHPCNITEEDYQPLMKLGTQT
VPCNKILLWSRIKDLAHQFTQVQRDMFTLEDTLLGYLADDLTWCGEFNTSKINYQSCP
DWRKDCSNNPVSVFWKTVSRRFAEAACDVVHVMLNGSRSKIFDKNSTFGSVEVHNLQ
PEKVQTLEAWVIHGGREDSRDLCQDPTIKELESIISKRNIQFSCKNIYRPDKFLQCVKNPE
DSSCTSEI

**CD38 *Macaca fascicularis/Cynomolgus/Crab eating macaque* (Accession AAT36330.1; SEQ ID NO:2)**

MANCEFSPVSGDKPCCRLSRRAQVCLGVCLLVLLILVVVVAVVLPRWRQQWSGSGTTS
RFPETVLARCVKYTEVHPEMRHVDCQSVWDAFKGAFISKYPCNITEEDYQPLVKLGTQ
TVPCNKTLLWSRIKDLAHQFTQVQRDMFTLEDMLLGYLADDLTWCGEFNTFEINYQSC
PDWRKDCSNNPVSVFWKTVSRRFAETACGVVHVMLNGSRSKIFDKNSTFGSVEVHNL
QPEKVQALEAWVIHGGREDSRDLCQDPTIKELESIISKRNIRFFCKNIYRPDKFLQCVKN
PEDSSCLSGI

FIGURE 5
A
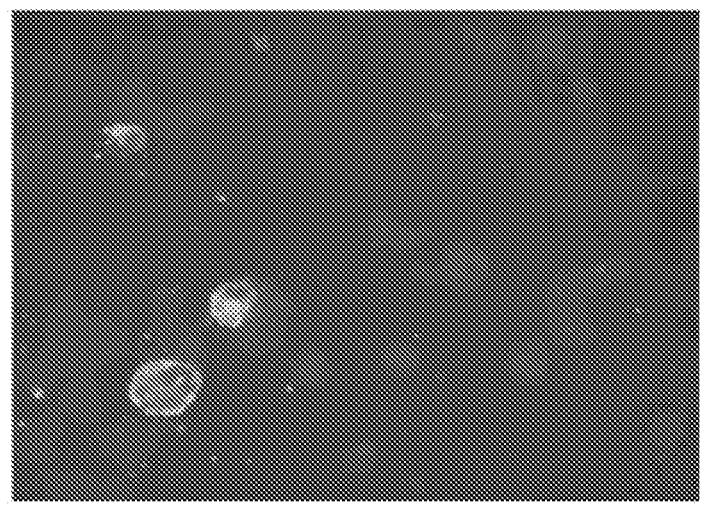
40X
B
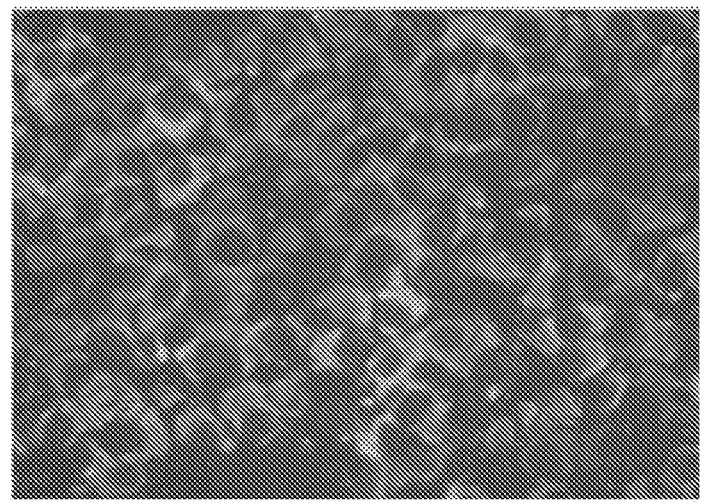
40X

FIGURE 6
A
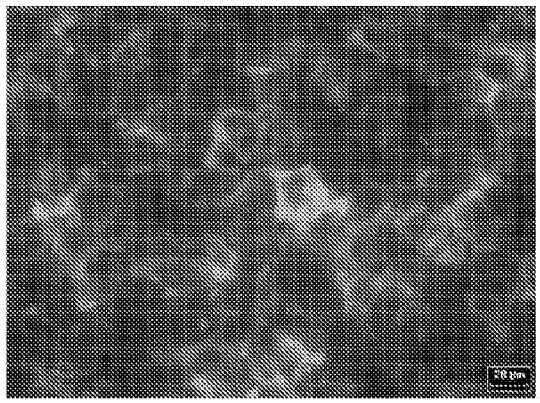
B
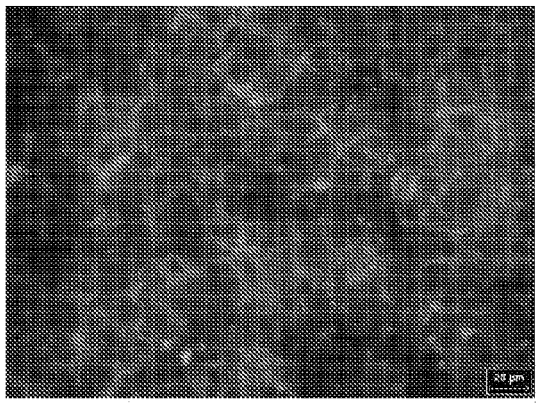
C
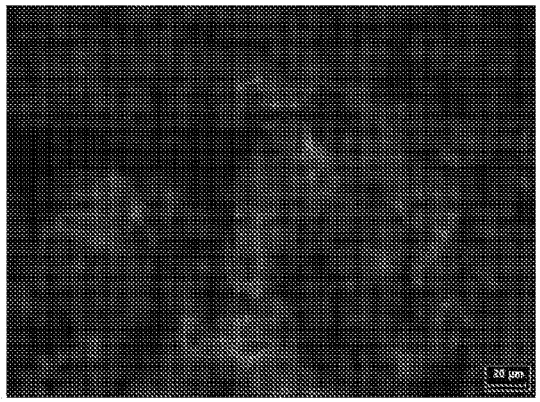
D
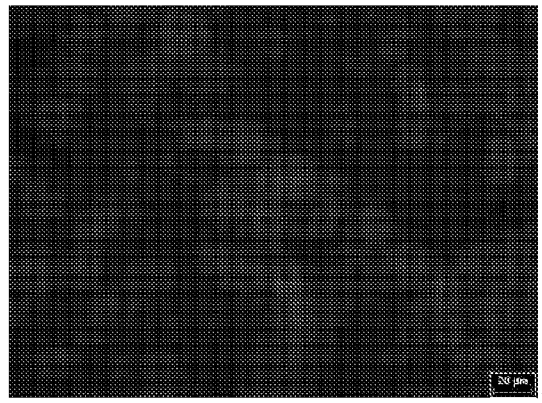

FIGURE 9
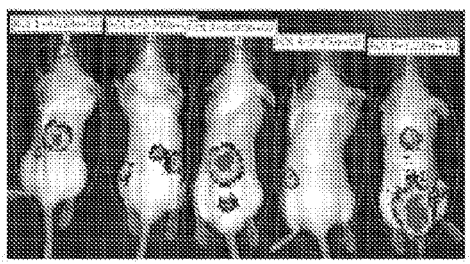
Saline
2mg/kg Palivizumab
0.1 mg/kg BM1
0.1 mg/kg BM2
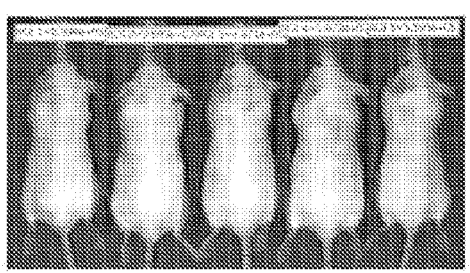
0.1 mg/kg TSF #19
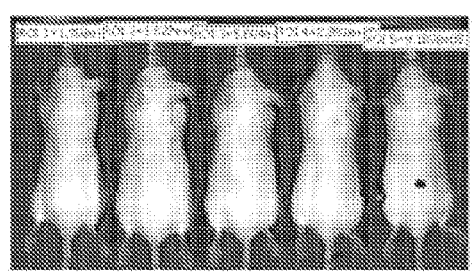
0.1 mg/kg TSF #79

FIGURE 11C
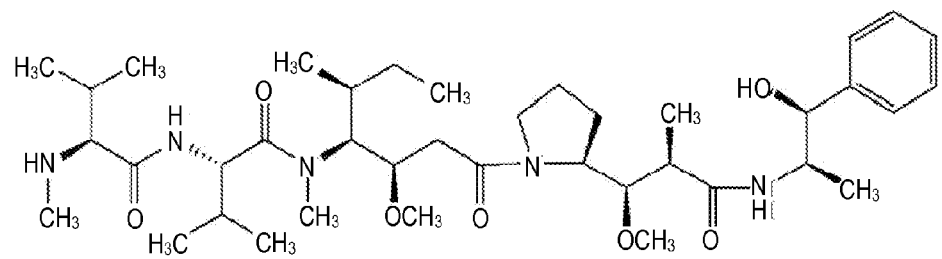
(XI)
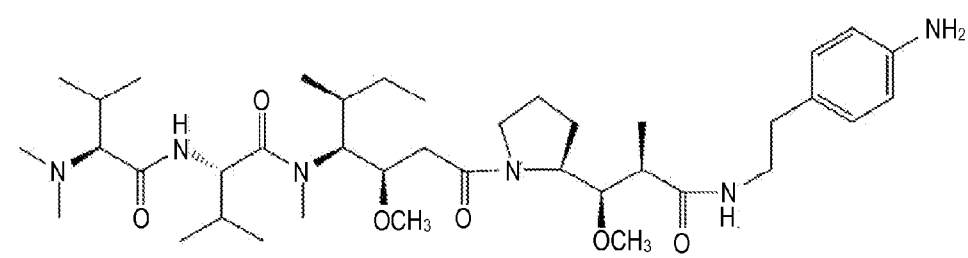
(XII)
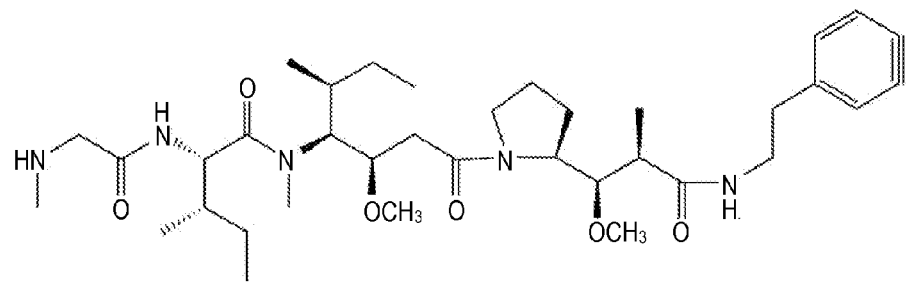
(XIII)
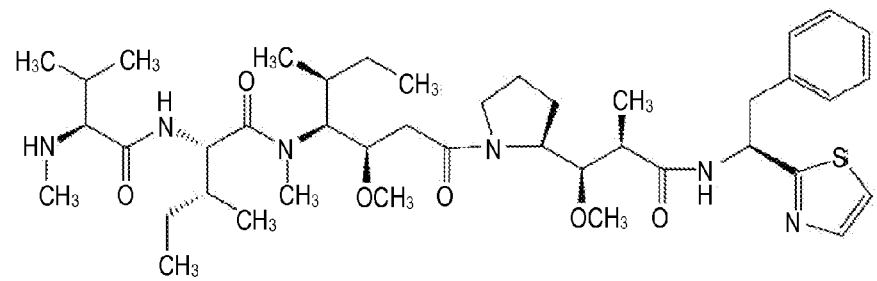
(XIV)

FIGURE 11D
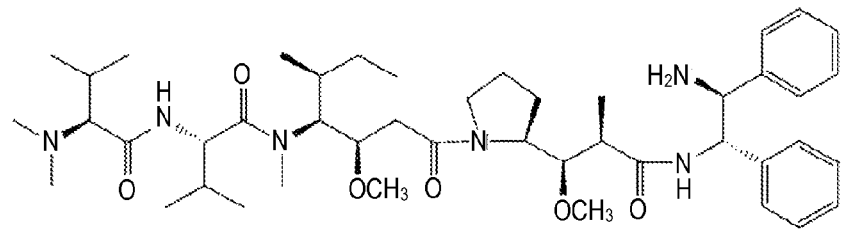
(XV)
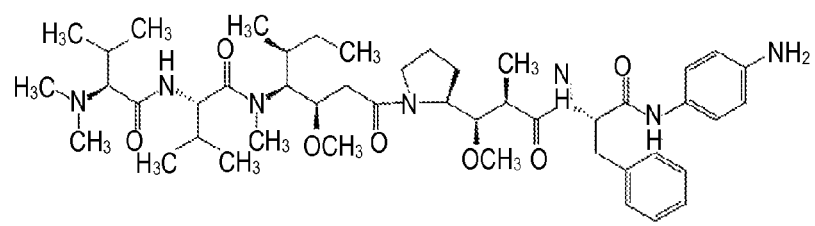
(XVI)
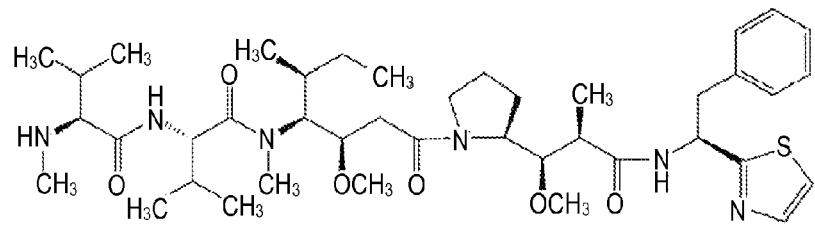
(XVII)
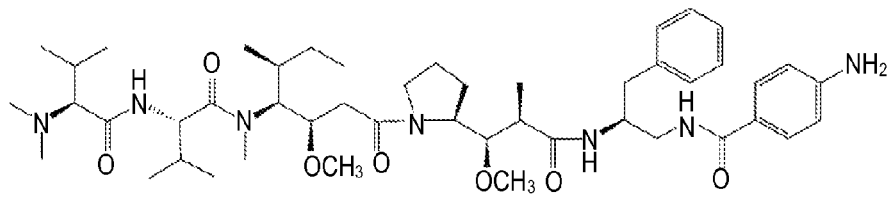
(XVIII)
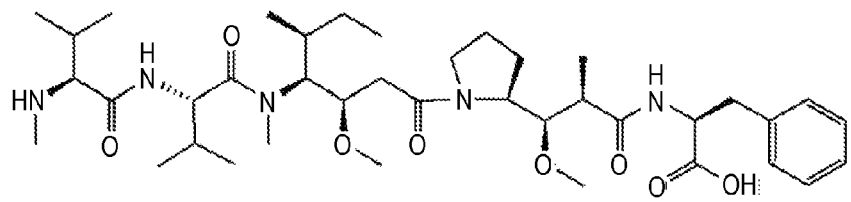
(XIX)

FIGURE 11E
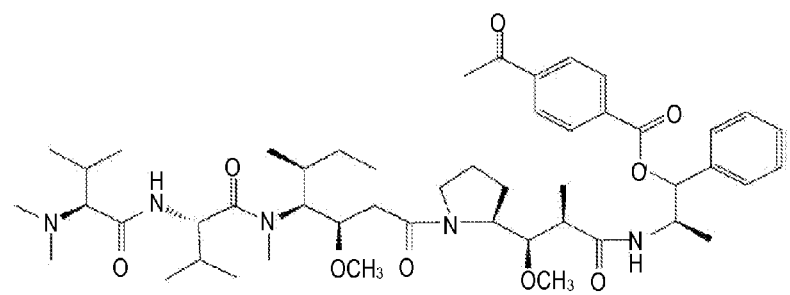
(XX)
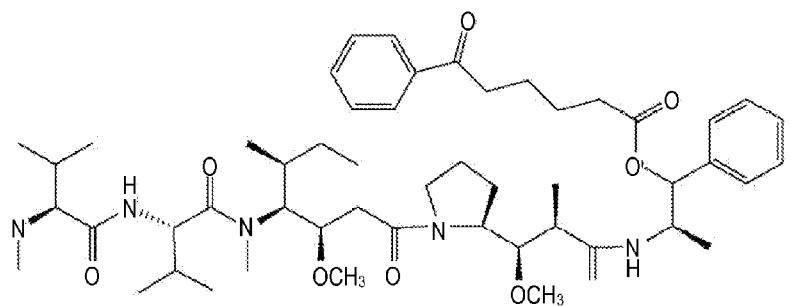
(XXI)

FIGURE 12

| BM2 | | BM1 | | TSF19 | | TSF79 | |
|---|---|---|---|---|---|---|---|
| E | 76 | N | 120 | G | 91 | K | 121 |
| H | 79 | K | 121 | E | 103 | F | 135 |
| E | 104 | F | 135 | E | 104 | Q | 139 |
| Q | 107 | Q | 139 | D | 105 | D | 141 |
| M | 110 | D | 141 | Q | 107 | M | 142 |
| K | 111 | D | 202 | M | 110 | E | 239 |
| L | 112 | V | 203 | K | 111 | W | 241 |
| G | 113 | H | 205 | T | 114 | S | 274 |
| T | 114 | Q | 236 | Q | 115 | C | 275 |
| Q | 115 | T | 237 | T | 148 | K | 276 |
| T | 116 | E | 239 | V | 192 | F | 284 |
| V | 117 | W | 241 | R | 194 | V | 288 |
| C | 119 | Q | 272 | R | 195 | K | 289 |
| T | 148 | F | 273 | F | 196 | N | 290 |
| L | 150 | S | 274 | E | 198 | P | 291 |
| T | 191 | C | 275 | A | 199 | E | 292 |
| V | 192 | K | 276 | H | 228 | D | 293 |
| R | 194 | F | 284 | N | 229 | S | 294 |
| R | 195 | P | 291 | Q | 231 | | |
| F | 196 | E | 292 | E | 233 | | |
| E | 198 | T | 297 | K | 234 | | |
| A | 199 | S | 298 | | | | |
| Q | 231 | | | | | | |
| E | 233 | | | | | | |
| K | 234 | | | | | | |

CONJUGATED ANTI-CD38 ANTIBODIES

This application is a 371 National Phase application of PCT/US11/68244 filed Dec. 30, 2011, which claims benefit under 35 U.S.C. §119(e) to U.S. Ser. No. 61/428,699, filed Dec. 30, 2010; U.S. Ser. No. 61/470,382, filed Mar. 31, 2011; U.S. Ser. No. 61/470,406, filed Mar. 31, 2011; and U.S. Ser. No. 61/485,104, filed May 11, 2011, all entirely incorporated by reference.

BACKGROUND

CD38, also known as cyclic ADP ribose hydrolase, is a type II transmembrane glycoprotein with a long C-terminal extracellular domain and a short N-terminal cytoplasmic domain. CD38 is a member of a group of related membrane bound or soluble enzymes, comprising CD157 and Aplysia ADPR cyclase. This family of enzymes has the unique capacity to convert NAD to cyclic ADP ribose or nictotinic acid-adenine dinucleotide phosphate.

In addition, CD38 has been reported to be involved in $Ca^{2+}$ mobilization and in the signal transduction through tyrosine phosphorylation of numerous signaling molecules, including phospholipase Cγ, ZAP-70, syk, and c-cbl. Based on these observations, CD38 was proposed to be an important signaling molecule in the maturation and activation of lymphoid cells during their normal development.

Among hematopoietic cells, an assortment of functional effects have been ascribed to CD38 mediated signalling, including lymphocyte proliferation, cytokine release, regulation of B and myeloid cell development and survival, and induction of dendritic cell maturation.

Yet, the exact role of CD38 in signal transduction and hematopoiesis remains unclear, since most of the signal transduction studies have used cell lines ectopically overexpressing CD38 and anti-CD38 monoclonal antibodies, which are non-physiological ligands.

The presumed natural ligand of CD38 is CD31 (PECAM-1; Platelet Endothelial Cell Adhesion Molecule-1). CD31 is a 130 kD member of the immunoglobulin superfamily which is expressed on the surface of circulating platelets, neutrophils, monocytes, and naïve B-lymphocytes. Functionally, CD31 is thought to act as an adhesion molecule. It has been suggested that the interaction of CD38 with CD31 may act in promoting survival of leukemia cells.

Animal models deficient for a single molecule have in many instances been fundamental tools for understanding the biological role of the molecule in the animal. The underlying assumption is that if the protein exerts a non-redundant function, then its complete lack will result in the complete loss of that function.

CD38 knockout mice have been generated. These animals show an almost complete loss of tissue associated NADase activity. Yet, these animals are viable, leading to the conclusion that CD38 and its activities are not necessary for life. These mice do however exhibit a defect in their innate immunity and a reduced T-cell dependent humoral response.

In contrast to the results in mice, in humans there is strong circumstantial evidence that the absence of CD38 is incompatible with life. Analysis of more than 5,000 blood samples from newborns failed to identify a single $CD38^-$ individual; suggesting that unlike mice, CD38 is necessary for survival. Thus, it is not clear that the observations made in mice concerning CD38 function can be extrapolated to humans.

CD38 is upregulated in many hematopoeitic malignancies and in cell lines derived from various hematopoietic malignancies including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are $CD38^-$ (FIG. 1).

In spite of the recent progress in the discovery and development of anti-cancer agents, many forms of cancer involving CD38-expressing tumors still have a poor prognosis. Thus, there is a need for improved methods for treating such forms of cancer.

BRIEF SUMMARY OF THE INVENTION

Provided herein are reagents and methods for binding to CD38 and methods, for treating CD38 associated diseases and detecting CD38 using CD38-specific binding agents including antibodies specific for CD38. For therapeutic purposes, the antibodies of the invention include a conjugated drug moiety, as described below. For diagnostic purposes, the antibodies of the invention can optionally include a detectable label.

Accordingly, in some embodiments, an isolated antibody specific for human CD38 (SEQ ID NO:1) and cynomolgus CD38 (SEQ ID NO:2) is described. This antibody is composed of a heavy chain variable region and a light chain variable region, wherein the heavy chain variable region is composed of three complementary determining regions (CDRs), HCDR1, HCDR2, and HCDR3, and wherein the light chain variable region is also composed of three CDRs, LCDR1, LCDR2, and LCDR3. The sequences of the CDRs are represented by: HCDR1 (SEQ ID NO:3), HCDR2 (SEQ ID NO:4), HCDR3 (SEQ ID NO:5), LCDR1 (SEQ ID NO:6), LCDR2 (SEQ ID NO:7) and LCDR3 (SEQ ID NO:8). In some embodiments, the antibody further comprises a conjugated drug moiety.

In other embodiments, the isolated antibody is composed of a heavy chain variable region, wherein the sequence of heavy chain variable region is encompassed by SEQ ID NO:9. In other embodiments, the isolated antibody is composed of a light chain variable region, wherein the sequence of the light chain variable region is encompassed by SEQ ID NO:10. In some embodiments, the antibody further comprises a conjugated drug moiety.

In some embodiments, the isolated antibody is composed of a heavy chain variable region, wherein the sequence of heavy chain variable region is encompassed by SEQ ID NO:9. In other embodiments, the isolated antibody is composed of a light chain variable region, wherein the sequence of the light chain variable region is encompassed by SEQ ID NO:10. This combination of heavy chain variable region and light chain variable region is referred to as Ab79. In some embodiments, the antibody further comprises a conjugated drug moiety.

In some embodiments, the isolated antibody is composed of a heavy chain and a light chain, wherein the heavy chain sequence is encompassed by SEQ ID NO:11 and the light chain is encompassed by SEQ ID NO:12. In some embodiments, the antibody further comprises a conjugated drug moiety.

In some embodiments, the isolated antibody includes an Fc domain. In other embodiments, the Fc domain is a human Fc domain. In still other embodiments, the Fc domain is a variant Fc domain.

In some embodiments, an isolated nucleic acid encoding the heavy chain of SEQ ID NO:11 is provided. In other embodiments, an isolated nucleic acid encoding the light chain of SEQ ID NO:12 is provided.

In some embodiments, a host cell is provided, the host cell containing the isolated nucleic acid encoding the heavy chain of SEQ ID NO:11 and the isolated nucleic acid encoding the light chain of SEQ ID NO:12.

In some embodiments, a method of producing the antibody of the invention is provided. The method encompassing culturing a host cell containing the isolated nucleic acid encoding the heavy chain of SEQ ID NO:11 and the isolated nucleic acid encoding the light chain of SEQ ID NO:12 under conditions wherein the isolated nucleic acid(s) are expressed and an antibody is produced. The drug moiety is then attached to the antibody using chemistries standard in the art.

In some embodiments, an isolated antibody specific for human CD38 (SEQ ID NO:1) and cynomolgus CD38 (SEQ ID NO:2) is described. This antibody is composed of six CDRs, wherein each CDR of this antibody can differ from SEQ ID NO:3, SEQ ID NO:4, SEQ ID NO:5, SEQ ID NO:6, SEQ ID NO:7, and SEQ ID NO:8 by 0, 1, or 2 amino acid substitutions. In some embodiments, the antibody further comprises a conjugated drug moiety.

In other embodiments, an isolated antibody specific for human CD38 (SEQ ID NO:1) and cynomolgus CD38 (SEQ ID NO:2) is described. This antibody is composed of a heavy chain variable region and a light chain variable region, wherein the heavy chain variable region is composed of three complementary determining regions (CDRs), HCDR1, HCDR2, and HCDR3, and wherein the light chain variable region is also composed of three CDRs, LCDR1, LCDR2, and LCDR3. The sequences of the CDRs are represented by: HCDR1 (SEQ ID NO:13), HCDR2 (SEQ ID NO:14), HCDR3 (SEQ ID NO:15), LCDR1 (SEQ ID NO:16), LCDR2 (SEQ ID NO:17) and LCDR3 (SEQ ID NO:18). In some embodiments, the antibody further comprises a conjugated drug moiety.

In other embodiments, the isolated antibody is composed of a heavy chain variable region, wherein the sequence of heavy chain variable region is encompassed by SEQ ID NO:19. In other embodiments, the isolated antibody is composed of a light chain variable region, wherein the sequence of the light chain variable region is encompassed by SEQ ID NO:20. In some embodiments, the antibody further comprises a conjugated drug moiety.

In some embodiments, the isolated antibody is composed of a heavy chain variable region, wherein the sequence of heavy chain variable region is encompassed by SEQ ID NO:19. In other embodiments, the isolated antibody is composed of a light chain variable region, wherein the sequence of the light chain variable region is encompassed by SEQ ID NO:20. This combination of heavy chain variable region and light chain variable region is referred to as Ab19. In some embodiments, the antibody further comprises a conjugated drug moiety. In some embodiments, the antibody alternatively further comprises a detectable label to facilitate diagnosis.

In some embodiments, the isolated antibody is composed of a heavy chain and a light chain, wherein the heavy chain sequence is encompassed by SEQ ID NO:21 and the light chain is encompassed by SEQ ID NO:22. In some embodiments, the antibody further comprises a conjugated drug moiety.

In some embodiments, an isolated nucleic acid encoding the heavy chain of SEQ ID NO:21 is provided. In other embodiments, an isolated nucleic acid encoding the light chain of SEQ ID NO:22 is provided.

In some embodiments, a host cell is provided, the host cell containing the isolated nucleic acid encoding the heavy chain of SEQ ID NO:21 and the isolated nucleic acid encoding the light chain of SEQ ID NO:22.

In some embodiments, a method of producing the antibody of the invention is provided. The method encompassing culturing a host cell containing the isolated nucleic acid encoding the heavy chain of SEQ ID NO:21 and the isolated nucleic acid encoding the light chain of SEQ ID NO:22 under conditions wherein the isolated nucleic acid(s) are expressed and an antibody is produced. The drug moiety is then attached to the antibody using chemistries standard in the art.

In other embodiments, an isolated antibody specific for human CD38 (SEQ ID NO:1) and cynomolgus CD38 (SEQ ID NO:2) is described. This antibody is composed of six CDRs, wherein each CDR of this antibody can differ from SEQ ID NO:13, SEQ ID NO:14, SEQ ID NO:15, SEQ ID NO:16, SEQ ID NO:17, and SEQ ID NO:18 by 0, 1, or 2 amino acid substitutions.

In some embodiments, an isolated anti-CD38 antibody is provided that binds specifically to human CD38 (SEQ ID NO:1) and cynomolgus CD38 (SEQ ID NO:2), wherein the antibody binds to human CD38 with a KD of about $10^{-6}$, $10^{-7}$, $10^{-8}$, $10^{-9}$ or more and binds cynomolgus CD38 with a KD of about $10^{-6}$, $10^{-7}$, $10^{-8}$, $10^{-9}$ or more.

In some embodiments, antibodies that compete with Ab79 and/or Ab19 for binding to human CD38 and/or cynomolgus CD38 are provided.

These and other embodiments, features and potential advantages will become apparent with reference to the following description and drawings.

BRIEF DESCRIPTION OF THE DRAWINGS

FIG. 2 shows the heavy and light chain sequences of Ab79 and Ab19.

FIG. 3 depicts the sequences of human and cynomolgus CD38.

FIG. 5 shows detection of Ab79 binding to bone marrow samples from Multiple Myeloma (MM) patients. (A) Immunofluorescent Ab79 staining of normal bone marrow (B) Representative immunofluorescent Ab79 staining of bone marrow from a MM patient. The epitope recognized by Ab79 was strongly expressed in approximately 50% or more of the cells in all multiple myeloma samples examined whereas in normal bone marrow approximately 10% or less of the cells.

FIG. 6 depicts the binding of Ab79 to various cell lines as detected by immunofluorescence. (A) MOLP-8 (B) Daudi (C) RPMI (D) MCF7.

FIG. 9 depicts visualization of lymphoma dissemination in mice treated with Ab19, Ab79, and benchmark antibodies BM1 and BM2.

FIGS. 11, 11A, 11B, 11C, 11D, and 11E depict a number of different ADC embodiments. As described herein, the linker moieties may change, including the composition of the amino acids, the self-immolative linkers, etc.

FIG. 12 shows the epitopes of human CD38 that bind to each of the antibodies, Benchmark 1 and 2, Ab19 and Ab79.

DETAILED DESCRIPTION OF THE INVENTION

Overview

Figure 1:
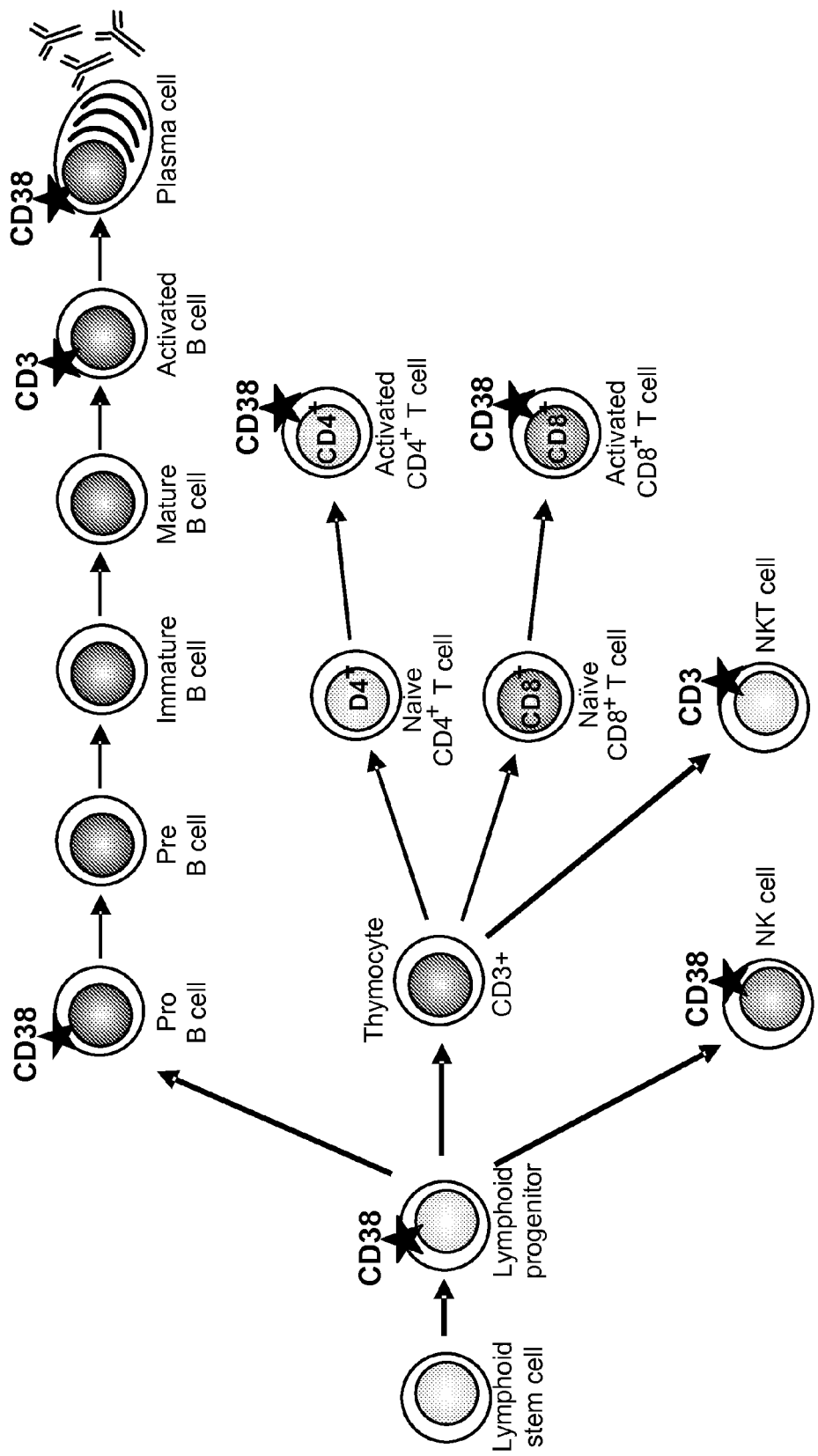
FIG. 1 depicts the CD38 Expression Profile on Lymphoid Lineage Cells. CD38 expression has been identified on pro-B cells ($CD34^+CD19^+CD20^-$), activated B cells ($CD19^+CD20^+$), plasma cells ($CD138^+CD19^-CD20^-$), activated $CD4^+$ and $CD8^+$ T cells, NKT cells ($CD3^+CD56^+$) and NK cells ($CD56^+CD16^+$). In addition, CD38 expression is found on lymphoid progenitor cells ($CD34^+CD45RA^+CD10^+CD19^-$) but not the lymphoid stem cell.

The extracellular domain of CD38 has been shown to possess bifunctional enzyme activity, having both ADP-ribosyl cyclase as well as ADP-ribosyl hydrolase activities. Thus, CD38 can catalyze the conversion of NAD$^+$ to cADPR (cyclase) and can further hydrolyze it to ADP-ribose (hydrolase). cADPR is involved in the mobilization of calcium from intracellular stores which is a second messenger activity important for cellular proliferation, differentiation, and apoptosis.

Increased expression of CD38 has been documented in a variety of diseases of hematopoietic origin and has been described as a negative prognostic marker in chronic lymphoblastic leukemia. Such diseases include but are not restricted to, multiple myeloma (Jackson et al. (1988)), chronic lymphoblastic leukemia (Moribito et al. (2001), Jelinek et al. (2001), Chevalier et al. (2002), Dürig et al. (2002)), B-cell chronic lymphocytic leukemia, acute lymphoblastic leukemia (Keyhani et al (2000)) including B-cell acute lymphocytic leukemia, Waldenstrom macroglobulinemia, primary systemic amyloidosis, mantle-cell lymphoma, pro-lymphocytic/myelocytic leukemia, acute myeloid leukemia (Keyhani et al. (1993)), chronic myeloid leukemia (Marinov et al. (1993)), follicular lymphoma, NK-cell leukemia and plasma-cell leukemia. As such, CD38 provides a useful target in the treatment of diseases of the hematopoietic system.

Several anti-CD38 antibodies are in clinical trials for the treatment of CD38-associated cancers (herein referred to as "Benchmark 1 and Benchmark 2"). Accordingly, antibodies to CD38 with therapeutic effect and/or diagnostic applications are useful. The invention provides two different anti-CD38 sets of CDRs that bind to different epitopes of CD38, and which bind both human and cynomolguso forms of CD38, and antibodies that contain these CDRs. The antibodies further comprise drug/linker conjugates as discussed herein.

One advantage, not seen in some of the anti-CD38 antibodies in clinical testing, is the ability to bind to cynomolgus CD38, as these primates find use in preclinical testing, and thus can lead to early evaluation of dosing, toxicity, efficacy, etc.

CD38 Proteins

Accordingly, the present invention provides isolated anti-CD38 antibodies that specifically bind human CD38 protein (and, as described below, additionally and preferably specifically bind primate CD38 protein). As is known in the art, CD38 proteins are found in a number of species. Of particular use in the present invention are antibodies that bind to both the human and primate CD38 proteins, particularly primates used in clinical testing, such as cynomolgus (*Macaca fascicularis*, Crab eating macaque, sometimes referred to herein as "cyno") monkeys. By "human CD38" or "human CD38 antigen" refers to the protein of SEQ ID NO:1 or a functional fraction, such as an epitope, as defined herein. In general, CD38 possesses a short intracytoplasmic tail, a transmembrane domain, and an extracellular domain, in specific embodiments, the antibodies of the invention bind to the extracellular part of the CD38 protein. By "cynomolgus CD38" herein is meant SEQ ID NO:2 which is 92% identical to human CD38.

Synonyms of CD38, include ADP ribosyl cyclase 1, cADPr hydrolase 1, Cd38-rs1, Cyclic ADP-ribose hydrolase 1, 1-19, and NIM-R5 antigen.

In some embodiments, the anti-CD38 Ab79 antibodies of the invention interact with CD38 at a number of amino acid residues including K121, F135, Q139, D141, M142, D202, V203, H205, Q236, E239, W241, S274, C275, K276, F284, C287, V288, K289, N290, P291, E292, D293. As outlined herein, other antibodies that interact with these residues also find use in therapeutic and diagnostic applications.

In some embodiments, the anti-CD38 antibodies of the present invention optionally (and in some cases preferably) do not bind to other members of the CD38 family such as CD157. For example, preferred embodiments herein do not bind to human CD157 of SEQ ID NO:23 (Genbank accession NP_004325).

Antibodies

The present invention provides anti-CD38 antibodies, generally therapeutic and/or diagnostic antibodies as described herein. Antibodies that find use in the present invention can take on a number of formats as described herein, including traditional antibodies as well as antibody derivatives, fragments and mimetics, described below. Essentially, the invention provides antibody structures that contain a set of 6 CDRs as defined herein (including small numbers of amino acid changes as described below).

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. It should be understood that therapeutic antibodies can also comprise hybrids of isotypes and/or subclasses.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5$^{th}$ Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)), with the EU number system used for the Fc region.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. For example, as shown herein, the two different antibodies referred to herein as "Ab19" and "Ab79" bind to different epitopes on the CD38 molecule.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning", as outlined in the Examples XRay crystallography studies as shown in the Examples has identified the amino acid residues that bind to the antibodies both of the invention (including Ab19 and Ab79) and the prior art (Benchmark 1 and Benchmark 2), as shown in FIG. 12.

In the present invention, Ab79 as outlined in the Examples, interacts with a number of amino acid residues of CD38 including K121, F135, Q139, D141, M142, E239, W241, S274, C275, K276, F284, V288, K289, N290, P291, E292 and D293. It should be noted that these residues are identical in both human and cyan monkeys, with the exception that S274 is actually F274 in cyan. These residues may represent the immunodominant epitope and/or residues within the footprint of the specifically antigen binding peptide.

In the present invention, Ab19 binds to a different epitope, including G91, E103, E1034, D105, Q107, M110, K111, T114, Q115, T148, V192, R194, R195, F196, A199, H228, N229, Q231, E233 and K234. It should be noted that these residues are identical in both human and cyan monkeys, with the exception that M110 is V110 in cyan and A199 is T199 in cyan.

Thus, in some embodiments, antibodies that compete with AB79 and Ab19 by binding at either of these epitopes can be used to treat autoimmune diseases. It should be noted that Ab79 and BM1 have some overlap; thus antibodies that compete with Ab79 and are not BM1 find use in the present invention.

Thus, the present invention provides antibodies that bind to both human and cyan CD38 and interact with at least 80%, 90%, 95% or 98% of these residues. Stated differently, the surface area of the interaction zone is no more than the area of these residues.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5$^{th}$ edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Structures that still rely In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242: 423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

Chimeric and Humanized Antibodies

In some embodiments, the antibody can be a mixture from different species, e.g. a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20): 4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16): 10678-10684; Rosok et al., 1996, J. Biol. Chem. 271(37):

22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169: 3076-3084, all entirely incorporated by reference.

In one embodiment, the antibodies of the invention can be multispecific antibodies, and notably bispecific antibodies, also sometimes referred to as "diabodies". These are antibodies that bind to two (or more) different antigens, or different epitopes on the same antigen. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. For instance, an isolated antibody that specifically binds to CD38 is substantially free of antibodies that specifically bind antigens other than CD38.

An isolated antibody that specifically binds to an epitope, isoform or variant of human CD38 or cynomolgus CD38 may, however, have cross-reactivity to other related antigens, for instance from other species, such as CD38 species homologs. Moreover, an isolated antibody may be substantially free of other cellular material and/or chemicals.

Isolated monoclonal antibodies, having different specificities, can be combined in a well defined composition. Thus for example the Ab79 and Ab19 can be combined in a single formulation, if desired.

The anti-CD38 antibodies of the present invention specifically bind CD38 ligands (e.g. the human and cynomolgus CD38 proteins of SEQ ID NOs:1 and 2. "Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

Antibody Modifications

The present invention further provides variant antibodies. That is, there are a number of modifications that can be made to the antibodies of the invention, including, but not limited to, amino acid modifications in the CDRs (affinity maturation), amino acid modifications in the Fc region, glycosylation variants, covalent modifications of other types, etc.

By "variant" herein is meant a polypeptide sequence that differs from that of a parent polypeptide by virtue of at least one amino acid modification. Amino acid modifications can include substitutions, insertions and deletions, with the former being preferred in many cases.

In general, variants can include any number of modifications, as long as the function of the protein is still present, as described herein. That is, in the case of amino acid variants generated with the CDRs of either Ab79 or Ab19, for example, the antibody should still specifically bind to both human and cynomolgus CD38. Similarly, if amino acid variants are generated with the Fc region, for example, the variant antibodies should maintain the required receptor binding functions for the particular application or indication of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications, with from 1-2, 1-3 and 1-4 also finding use in many embodiments.

It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 95% or up to 98 or 99% identity to the parent sequences (e.g. the variable regions, the constant regions, and/or the heavy and light chain sequences for Ab79 and/or Ab19). It should be noted that depending on the size of the sequence, the percent identity will depend on the number of amino acids.

By "amino acid substitution" or "substitution" herein is meant the replacement of an amino acid at a particular position in a parent polypeptide sequence with another amino acid. For example, the substitution S100A refers to a variant polypeptide in which the serine at position 100 is replaced with alanine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, the parent polypeptides herein are Ab79 and Ab19. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant, and by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, one or more amino acid modifications are made in one or more of the CDRs of the antibody (either Ab79 or Ab19). In general, only 1 or 2 or 3amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR can be independently and optionally combined with any other substitution.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10% to 50-100-150% or more, or from 1 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155:1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of Ab79 and Ab19. In addition, as outlined below, amino acid modifications can also independently and optionally be made in any region outside the CDRs, including framework and constant regions.

In some embodiments, variant antibodies of Ab79 and Ab19 that are specific for human CD38 (SEQ ID NO:1) and cynomolgus CD38 (SEQ ID NO:2) is described. This antibody is composed of six CDRs, wherein each CDR of this antibody can differ from SEQ ID NO:3, SEQ ID NO:4, SEQ ID NO:5, SEQ ID NO:6, SEQ ID NO:7, and SEQ ID NO:8 by 0, 1, or 2 amino acid substitutions. In other embodiments, the variant anti-CD38 antibody is composed of six CDRs, wherein each CDR of this antibody can differ from SEQ ID NO:13, SEQ ID NO:14, SEQ ID NO:15, SEQ ID NO:16, SEQ ID NO:17, and SEQ ID NO:18 by 0, 1, or 2 amino acid substitutions.

In some embodiments, the anti-CD38 antibodies of the invention are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in U.S. patent application Ser. No. 11/841,654 and references cited therein, US 2004/013210, US 2005/0054832, US 2006/0024298, US 2006/0121032, US 2006/0235208, US 2007/0148170, U.S. Ser. No. 12/341,769, U.S. Pat. No. 6,737,056, U.S. Pat. No. 7,670,600, U.S. Pat. No. 6,086,875 all of which are expressly incorporated by reference in their entirety, and in particular for specific amino acid substitutions that increase binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference). In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Glycosylation

Another type of covalent modification is alterations in glycosylation. In another embodiment, the antibodies disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function. A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (Potelligent® technology [Biowa, Inc., Princeton, N.J.]; GlycoMAb® glycosylation engineering technology [Glycart Biotechnology AG, Zürich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example 20090317869, hereby incorporated by reference in its entirety. Engineered glycoform typically refers to the different carbohydrate or oligosaccharide; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

Specific CDR and Variable Region Embodiments

The present invention provides a number of antibodies each with a specific set of CDRs (including, as outlined above, some amino acid substitutions). As outlined above, the antibodies can be defined by sets of 6 CDRs, by variable regions, or by full-length heavy and light chains, including the constant regions. In addition, as outlined above, amino acid substitutions may also be made. In general, in the context of changes within CDRs, due to the relatively short length of the CDRs, the amino acid modifications are generally described in terms of the number of amino acid modifications that may be made. While this is also applicable to the discussion of the number of amino acid modifications that can be introduced in variable, constant or full length sequences, in addition to number of changes, it is also appropriate to define these changes in terms of the "% identity". Thus, as described herein, antibodies included within the invention are 80, 85, 90, 95, 98 or 99% identical to the SEQ ID NOs listed herein.

In the context of the Ab79 antibody, the set of CDRs is as follows: the three CDRs of the heavy chain encompass HCDR1 SEQ ID NO:3 (HCDR1), SEQ ID NO:4 (HCDR2), and SEQ ID NO:5 (HCDR3), and the three CDRs of the light chain encompass SEQ ID NO:6 (LCDR1), SEQ ID NO:7 (LCDR2), and SEQ ID NO:8 (LCDR3).

In the context of Ab19, the set of CDRs is as follows: HCDR1 (SEQ ID NO:13), HCDR2 (SEQ ID NO:14), and HCDR3 (SEQ ID NO:15), and LCDR1 (SEQ ID NO:16), LCDR2 (SEQ ID NO:17), and LCDR3 (SEQ ID NO:18).

Specifically excluded from the present invention are the antibodies of SEQ ID NOs.: 24 and 25 (the heavy and light chains of Benchmark 1) and SEQ ID NOs.: 26 and 27 (the heavy and light chains of Benchmark 2). It should be noted that these antibodies are not cross reactive with cynomolgus CD38, discussed below.

The antibodies of the invention are cross reactive with human and cynomolgus CD38 and are thus species cross-reactive antibodies. A "species cross-reactive antibody" is an antibody that has a binding affinity for an antigen from a first mammalian species that is nearly the same as the binding affinity for a homologue of that antigen from a second mammalian species. Species cross-reactivity can be expressed, for example, as a ratio of the KD of an antibody for an antigen of the first mammalian species over the KD of the same antibody for the homologue of that antigen from a second mammalian species wherein the ratio is 1.1, 1.2, 1.3, 1.4, 1.5, 2, 5, 10, 15, up to 20. Alternatively or additionally, an antibody is "species cross reactive" when it shows therapeutic or diagnostic efficacy when administered to the second species. Thus, in the present case, the antibodies of the invention are cross reactive with cynomolgus CD38, show preclinical efficacy when administered to cynomolgus primates and thus are considered cross reactive.

In some embodiments, antibodies that compete with the antibodies of the invention (for example, with Ab79 and/or Ab19) for binding to human CD38 and/or cynomolgus CD38 are provided, but are not either BM1 or BM2 are included. Competition for binding to CD38 or a portion of CD38 by two or more anti-CD38 antibodies may be determined by any suitable technique, as is known in the art.

Competition in the context of the present invention refers to any detectably significant reduction in the propensity of an antibody of the invention (e.g. Ab79 or Ab19) to bind its particular binding partner, e.g. CD38, in the presence of the test compound. Typically, competition means an at least about 10-100% reduction in the binding of an antibody of the invention to CD38 in the presence of the competitor, as measured by standard techniques such as ELISA or Biacore® assays. Thus, for example, it is possible to set criteria for competitiveness wherein at least about 10% relative inhibition is detected; at least about 15% relative inhibition is detected; or at least about 20% relative inhibition is detected before an antibody is considered sufficiently competitive. In cases where epitopes belonging to competing antibodies are closely located in an antigen, competition may be marked by greater than about 40% relative inhibition of CD38 binding (e.g., at least about 45% inhibition, such as at least about 50% inhibition, for instance at least about 55% inhibition, such as at least about 60% inhibition, for instance at least about 65% inhibition, such as at least about 70% inhibition, for instance at least about 75% inhibition, such as at least about 80% inhibition, for instance at least about 85% inhibition, such as at least about 90% inhibition, for instance at least about 95% inhibition, or higher level of relative inhibition).

In some cases, one or more of the components of the competitive binding assays are labeled, as discussed below in the context of diagnostic applications.

It may also be the case that competition may exist between anti-CD38 antibodies with respect to more than one of CD38 epitope, and/or a portion of CD38, e.g. in a context where the antibody-binding properties of a particular region of CD38 are retained in fragments thereof, such as in the case of a well-presented linear epitope located in various tested fragments or a conformational epitope that is presented in sufficiently large CD38 fragments as well as in CD38.

Assessing competition typically involves an evaluation of relative inhibitory binding using an antibody of the invention, CD38 (either human or cynomolgus or both), and the test molecule. Test molecules can include any molecule, including other antibodies, small molecules, peptides, etc. The compounds are mixed in amounts that are sufficient to make a comparison that imparts information about the selectivity and/or specificity of the molecules at issue with respect to the other present molecules.

The amounts of test compound, CD38 and antibodies of the invention may be varied. For instance, for ELISA assessments about 5-50 µg (e.g., about 10-50 µg, about 20-50 µg, about 5-20 µg, about 10-20 µg, etc.) of the anti-CD38 antibody and/or CD38 targets are required to assess whether competition exists. Conditions also should be suitable for binding. Typically, physiological or near-physiological conditions (e.g., temperatures of about 20-40° C., pH of about 7-8, etc.) are suitable for anti-CD38: CD38 binding.

Often competition is marked by a significantly greater relative inhibition than about 5% as determined by ELISA and/or FACS analysis. It may be desirable to set a higher threshold of relative inhibition as a criteria/determinant of what is a suitable level of competition in a particular context (e.g., where the competition analysis is used to select or screen for new antibodies designed with the intended function of blocking the binding of another peptide or molecule binding to CD38 (e.g., the natural binding partners of CD38 such as CD31, also called CD31 antigen, EndoCAM, GPIIA, PECAM-1, platelet/endothelial cell adhesion molecule or naturally occurring anti-CD38 antibody).

In some embodiments, the anti-CD38 antibody of the present invention specifically binds to one or more residues or regions in CD38 but also does not cross-react with other proteins with homology to CD38, such as BST-1 (bone marrow stromal cell antigen-1) and MoS, also called CD157.

Typically, a lack of cross-reactivity means less than about 5% relative competitive inhibition between the molecules when assessed by ELISA and/or FACS analysis using sufficient amounts of the molecules under suitable assay conditions.

The disclosed antibodies may find use in blocking a ligand-receptor interaction or inhibiting receptor component interaction. The anti-CD38 antibodies of the invention may be "blocking" or "neutralizing." A "neutralizing antibody" is intended to refer to an antibody whose binding to CD38 results in inhibition of the biological activity of CD38, for example its capacity to interact with ligands, enzymatic activity, and/or signaling capacity. Inhibition of the biological activity of CD38 can be assessed by one or more of several standard in vitro or in vivo assays known in the art (see examples below).

"Inhibits binding" or "blocks binding" (for instance when referring to inhibition/blocking of binding of a CD38 binding partner to CD38) encompass both partial and complete inhibition/blocking. The inhibition/blocking of binding of a CD38 binding partner to CD38 may reduce or alter the normal level or type of cell signaling that occurs when a CD38 binding partner binds to CD38 without inhibition or blocking. Inhibition and blocking are also intended to include any measurable decrease in the binding affinity of a CD38 binding partner to CD38 when in contact with an anti-CD38 antibody, as compared to the ligand not in contact with an anti-CD38 antibody, for instance a blocking of binding of a CD38 binding partner to CD38 by at least about 10%, 20%, 30%, 40%, 50%, 60%, 70%, 80%, 90%, 99%, or 100%.

The disclosed anti-CD38 antibodies may also inhibit cell growth. "Inhibits growth" includes any measurable decrease in the cell growth when contacted with a an anti-CD38 antibody, as compared to the growth of the same cells not in contact with an anti-CD38 antibody, for instance an inhibition of growth of a cell culture by at least about 10%, 20%, 30%, 40%, 50%, 60%, 70%, 80%, 90%, 99%, or 100%.

Methods for Producing the Antibodies of the Invention

The present invention further provides methods for producing the disclosed anti-CD38 antibodies. These methods encompass culturing a host cell containing isolated nucleic acid(s) encoding the antibodies of the invention. As will be appreciated by those in the art, this can be done in a variety of ways, depending on the nature of the antibody. In some embodiments, in the case where the antibodies of the invention are full length traditional antibodies, for example, a heavy chain variable region and a light chain variable region under conditions such that an antibody is produced and can be isolated.

In general, nucleic acids are provided that encode the antibodies of the invention. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are described, for example, in Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

Antibody drug conjugates as described herein are made as is known in the art, including techniques utilized by Seattle Genetics (see for example U.S. Pat. Nos. 8,067,546, 8,039,273, 7,989,434, 7,851,437, 7,837,980 and 7,829,531, all of which are expressly incorporated in their entirety by reference, with particular reference to drugs, linkers and methods of conjugation), Syntarga (see for example U.S. Pat. Nos. 7,705,045 and 7,223,837, all of which are expressly incorporated in their entirety by reference, with particular reference to drugs, linkers and methods of conjugation), Medarex (see for example U.S. Pat. Nos. 8,034,959, 8,034,787, 7,968,586, 7,847,105, all of which are expressly incorporated in their entirety by reference, with particular reference to drugs, linkers and methods of conjugation), and others well known in the art.

Applications and Indications

Once made, the antibodies of the invention find use in a variety of applications, including diagnosis of CD38-related diseases and treatment thereof.

CD38 Related Conditions

In one aspect, the invention provides methods of treating a condition associated with proliferation of cells expressing CD38, comprising administering to a patient a pharmaceutically effective amount of a disclosed antibody. In certain embodiments, the condition is cancer, and in particular embodiments, the cancer is hematological cancer. In other particular embodiments, the condition is multiple myeloma, chronic lymphoblastic leukemia, chronic lymphocytic leukemia, plasma cell leukemia, acute myeloid leukemia, chronic myeloid leukemia, B-cell lymphoma, or Burkitt's lymphoma.

It is known in the art that certain conditions are associated with cells that express CD38, and that certain conditions are associated with the overexpression, high-density expression, or upregulated expression of CD38 on the surfaces of cells. Whether a cell population expresses CD38 or not can be determined by methods known in the art, for example flow cytometric determination of the percentage of cells in a given population that are labelled by an antibody that specifically binds CD38 or immunohistochemical assays, as are generally described below for diagnostic applications. For example, a population of cells in which CD38 expression is detected in about 10-30% of the cells can be regarded as having weak positivity for CD38; and a population of cells in which CD38 expression is detected in greater than about 30% of the cells can be regarded as definite positivity for CD38 (as in Jackson et al. (1988), Clin. Exp. Immunol. 72: 351-356), though other criteria can be used to determine whether a population of cells expresses CD38. Density of expression on the surfaces of cells can be determined using methods known in the art, such as, for example, flow cytometric measurement of the mean fluorescence intensity of cells that have been fluorescently labelled using antibodies that specifically bind CD38.

In some embodiments, the compositions and methods of the invention are applied to a cancer such as a "hematologic cancer," a term that refers to malignant neoplasms of blood-forming tissues and encompasses leukemia, lymphoma and multiple myeloma. Non-limiting examples of conditions associated with CD38 expression include but are not limited to, multiple myeloma (Jackson et al. (1988), Clin. Exp. Immunol. 72: 351-356), B-cell chronic lymphocytic leukemia (B-CLL) Dürig et al. (2002), Leukemia 16: 30-5; Morabito et al. (2001), Leukemia Research 25: 927-32; Marinov et al. (1993), Neoplasma 40(6): 355-8; and Jelinek et al. (2001), Br. J. Haematol. 115: 854-61), acute lymphoblastic leukemia (Keyhani et al. (1999), Leukemia Research 24: 153-9; and Marinov et al. (1993), Neoplasma 40(6): 355-8), chronic myeloid leukemia (Marinov et al. (1993), Neoplasma 40(6): 355-8), acute myeloid leukemia (Keyhani et al. (1999), Leukemia Research 24: 153-9), chronic lymphocytic leukemia (CLL), chronic myelogenous leukemia or chronic myeloid leukemia (CML), acute myelogenous leukemia or acute myeloid leukemia (AML), acute lymphocytic leukemia (ALL), hairy cell leukemia (HCL), myelodysplastic syndromes (MDS) or chronic myelogenous leukemia (CML-BP) in blastic and all subtypes of these leukemias which are defined by morphological, histochemical and immunological techniques that are well known by those of skill in the art.

"Neoplasm" or "neoplastic condition" refers to a condition associated with proliferation of cells characterized by a loss of normal controls that results in one ore more symptoms including, unregulated growth, lack of differentiation, local tissue invasion, and metastasis.

In some embodiments of the invention, the hematologic cancer is a selected from the group of Chronic Lymphocytic Leukemia (CLL), Chronic Myelogenous Leukemia (CML), Acute Myelogenous Leukemia (AML), and Acute Lymphocytic Leukemia (ALL).

Furthermore, it is known in the art that CD38 expression is a prognostic indicator for patients with conditions such as, for example, B-cell chronic lymphocytic leukemia (Dürig et al. (2002), *Leukemia* 16: 30-5; and Morabito et al. (2001), *Leukemia Research* 25: 927-32) and acute myelogenous leukemia (Keyhani et al. (1999), *Leukemia Research* 24: 153-9).

CLL is the most common leukemia of adults in the Western world. CLL involves clonal expansion of mature-appearing lymphocytes involving lymph nodes and other lymphoid tissues with progressive infiltration of bone marrow and presence in the peripheral blood. The B-cell form (B-CLL) represents almost all cases.

B-CLL

B-CLL is an incurable disease characterized by a progressive increase of anergic monoclonal B lineage cells that accumulate in the bone marrow and peripheral blood in a protracted fashion over many years. The expression of CD38 is regarded as an independent poor prognostic factor for B-CLL. Hamblin et al., Blood 99:1023-9 (2002).

Today's standard therapy of B-CLL is palliative and is mainly carried out with the cytostatic agent chlorambucil or fludarabine. When relapses occur, a combination therapy using fludarabine, cyclophosphamide in combination with rituximab (monoclonal antibody against CD20) or campath (monoclonal antibody against CD52) is often initiated. Thus, there is a critical unmet medical need for the treatment of B-CLL. In some embodiments, methods for treating B-CLL using the disclosed anti-CD38 antibodies are provided (and, as outlined below, this may be done using combination therapies including optionally and independently any of the above drugs).

B-CLL is characterized by two subtypes, indolent and aggressive. These clinical phenotypes correlate with the presence or absence of somatic mutations in the immunoglobulin heavy-chain variable region (IgVH) gene. As used herein, indolent B-CLL refers to a disorder in a subjects having mutated IgVH gene and/or presenting with one or more clinical phenotypes associated with indolent B-CLL. As used herein, the phrase aggressive B-CLL refers to a disorder in a subject having unmutated IgVH and/or presenting with one or more clinical phenotypes associated with aggressive B-CLL.

Multiple Myeloma

Multiple myeloma is a malignant disorder of the B cell lineage characterized by neoplastic proliferation of plasma cells in the bone marrow. Current treatment regimens exhibit moderate response rates. However, only marginal changes in overall survival are observed and the median survival is approximately 3 years. Thus, there is a critical unmet medical need for the treatment of multiple myeloma. In some embodiments, methods for treating multiple myeloma using the disclosed antibodies are provided.

CD38 is highly expressed on plasma cells which are terminally differentiated B cells.

Proliferation of myeloma cells causes a variety of effects, including lytic lesions (holes) in the bone, decreased red blood cell number, production of abnormal proteins (with attendant damage to the kidney, nerves, and other organs), reduced immune system function, and elevated blood calcium levels (hypercalcemia).

Currently treatment options include chemotherapy, preferably associated when possible with autologous stem cell transplantation (ASCT).

Monoclonal Gammopathy of Undetermined Significance and Smoldering Multiple Myeloma In some embodiments, methods for treating monoclonal gammopathy using the disclosed antibodies are provided. In other embodiments, methods for treating smoldering multiple myeloma using the disclosed antibodies are provided.

Monoclonal gammopathy of undetermined significance (MGUS) and smoldering multiple myeloma (SMM) are asymptomatic, pre-malignant disorders characterized by monoclonal plasma cell proliferation in the bone marrow and absence of end-organ damage.

Smoldering multiple myeloma (SMM) is an asymptomatic proliferative disorder of plasma cells with a high risk of progression to symptomatic, or active multiple myeloma (N. Engl. J. Med. 356(25): 2582-2590 (2007)).

International consensus criteria defining SMM were adopted in 2003 and require that a patient have a M-protein level of >30 g/L and/or bone marrow clonal plasma cells >10% (Br. J. Haematol. 121: 749-57 (2003)). The patient must have no organ or related tissue impairment, including bone lesions or symptoms (Br. J. Haematol. 121: 749-57 (2003)).

Recent studies have identified two subsets of SMM; i) patients with evolving. disease and ii) patients with non-evolving disease (Br. J. Haematol. 121: 631-636 (2003)). International consensus criteria defining MGUS require that a patient have a M-protein level of <30 g/L, bone marrow plasma cells <10% and the absence of organ or related tissue impairment, including bone lesions or symptoms (Br. J. Haematol. 121: 749-57 (2003)).

SMM resembles monoclonal gammopathy of undetermined significance (MGUS) as end-organ damage is absent (N. Engl. J. Med. 356(25): 2582-2590 (2007)). Clinically, however, SMM is far more likely to progress to active multiple myeloma or amyloidosis at 20 years (78% probability for SMM vs. 21% for MGUS) (N. Engl. J. Med. 356(25): 2582-2590 (2007)).

FIGS. 11, 11A, 11B, 11C, 11D and 11E depict a number of different ADC embodiments. As described herein, the linker moieties may change, including the composition of the amino acids, the self-immolative linkers, etc.

Antibody-Drug Conjugates

In some embodiments, the anti-CD38 antibodies of the invention are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety Thus the invention provides anti-CD38 antibodies conjugated to drugs. Generally, conjugation is done by covalent attachment to the antibody, as further described below, and generally relies on a linker, often a peptide linkage (which, as described below, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug:antibody. As will be appreciated by those in the art, the actual number is an average.

Thus the invention provides anti-CD38 antibodies conjugated to drugs. As described below, the drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in the present invention include cytotoxic drugs, particularly those which are used for cancer therapy. Such drugs include, in general, DNA damaging agents, antimetabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of an anti-CD38 antibody and one or more small molecule toxins, such as a maytansinoids, dolastatins, auristatins, a trichothecene, calicheamicin, and CC1065, and the derivatives of these toxins that have toxin activity, are contemplated.

Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR) (U.S. Pat. No. 4,331,598); C-14-hydroxymethyl or acyloxymethyl (CH2OH or CH2OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. No. 5,416,064, WO/01/24763, U.S. Pat. Nos. 7,303,749, 7,601,354, U.S. Ser. No. 12/631,508, WO02/098883, U.S. Pat. Nos. 6,441,163, 7,368,565, WO02/16368 and WO04/1033272, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Auristatins and Dolastatins

In some embodiments, the ADC comprises an anti-CD38 antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238648, the disclosure of which is expressly incorporated by reference in its entirety.

Figure 10:
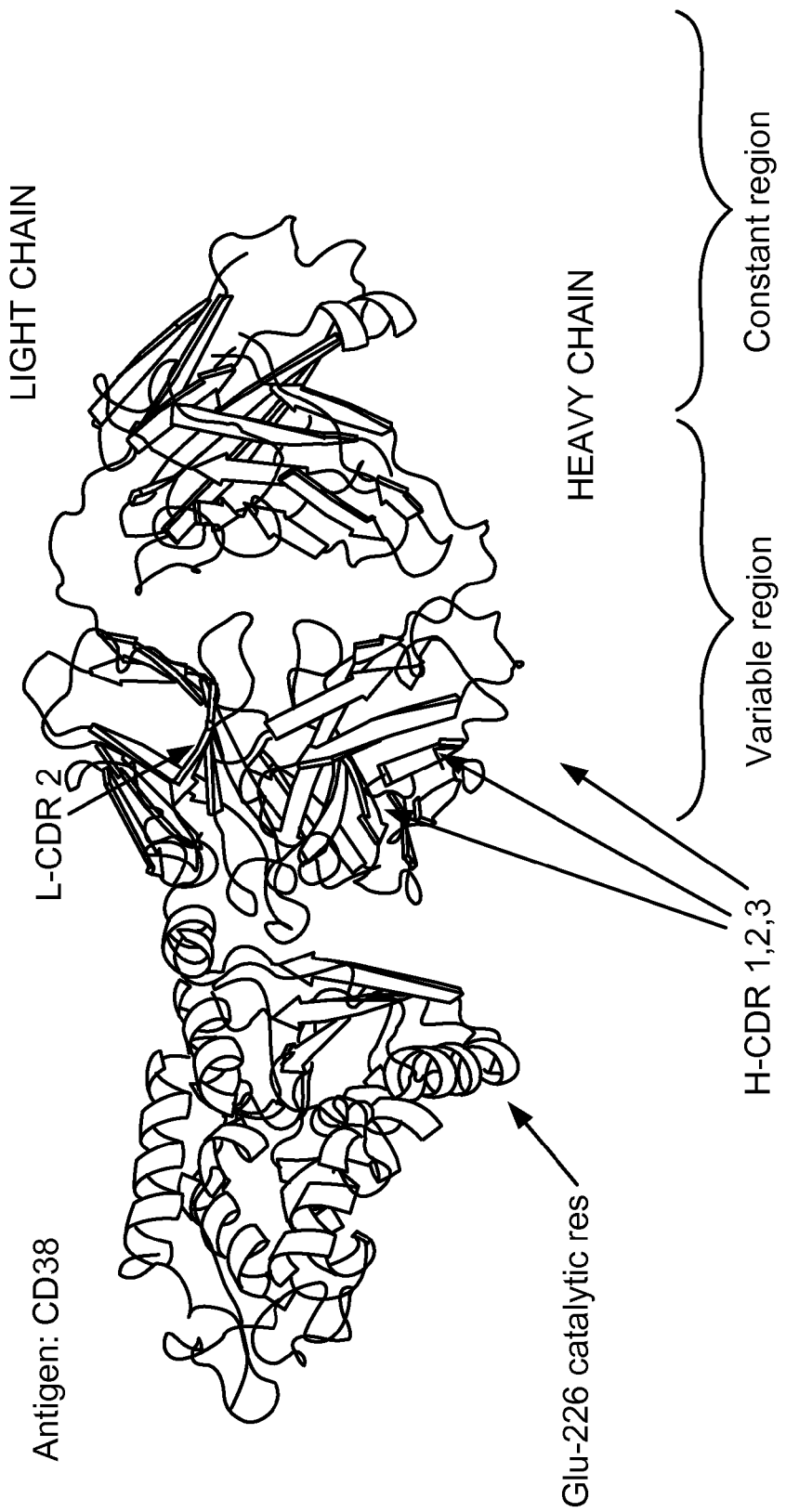
FIG. 10 depicts the binding of Ab79 to CD38 based on X-ray crystallography data.
Figure 11:
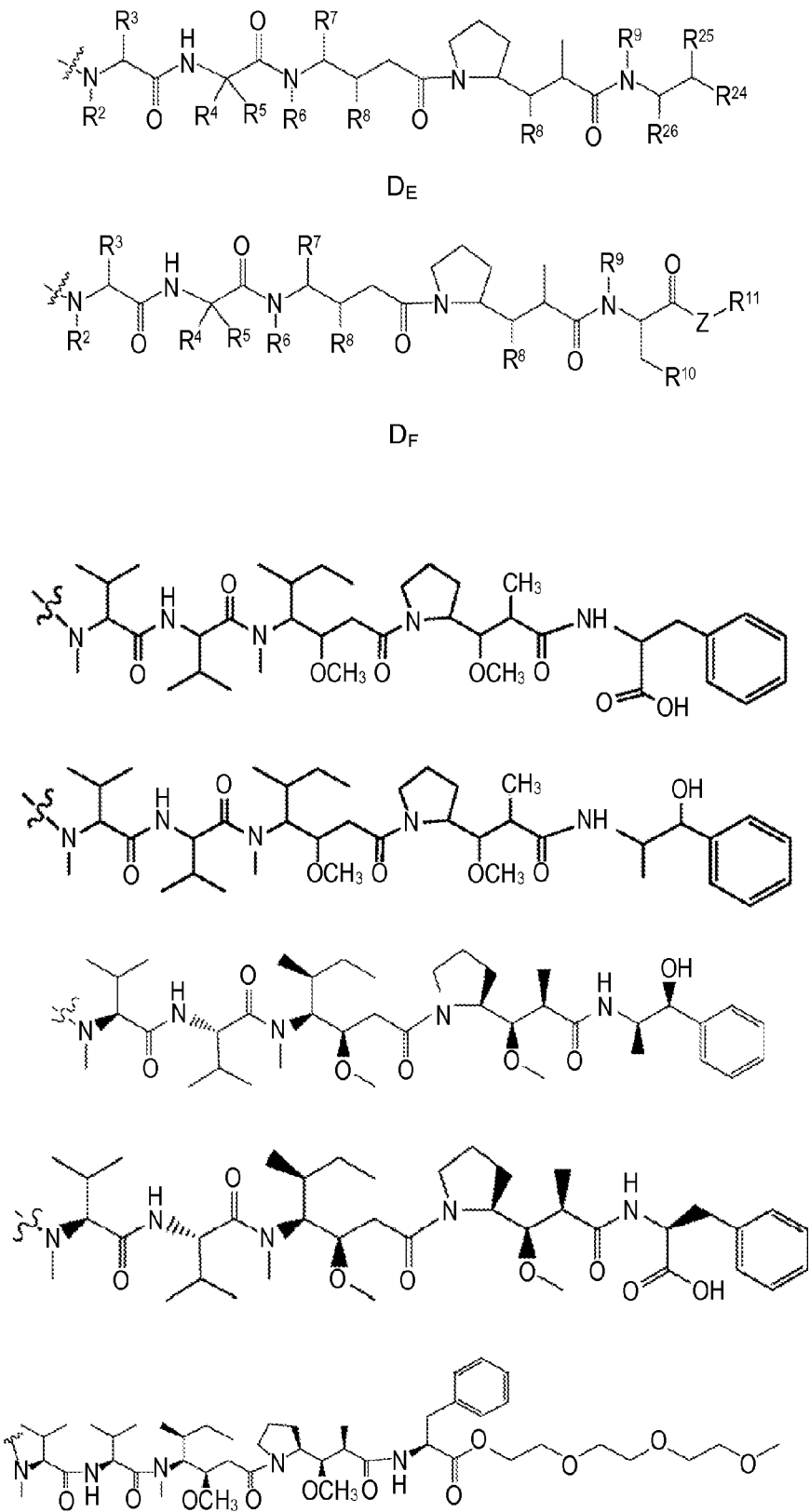
Figure 11A:
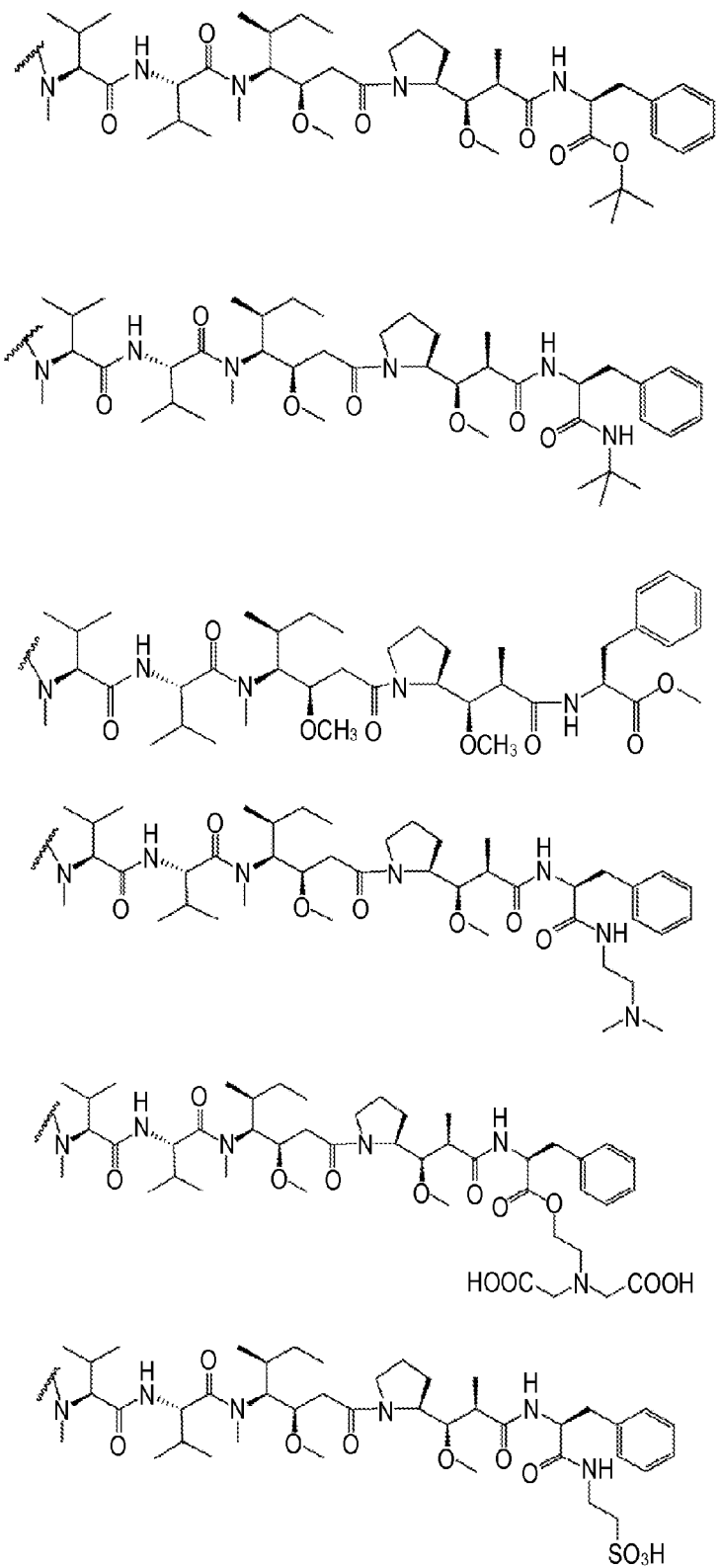
Figure 11B:
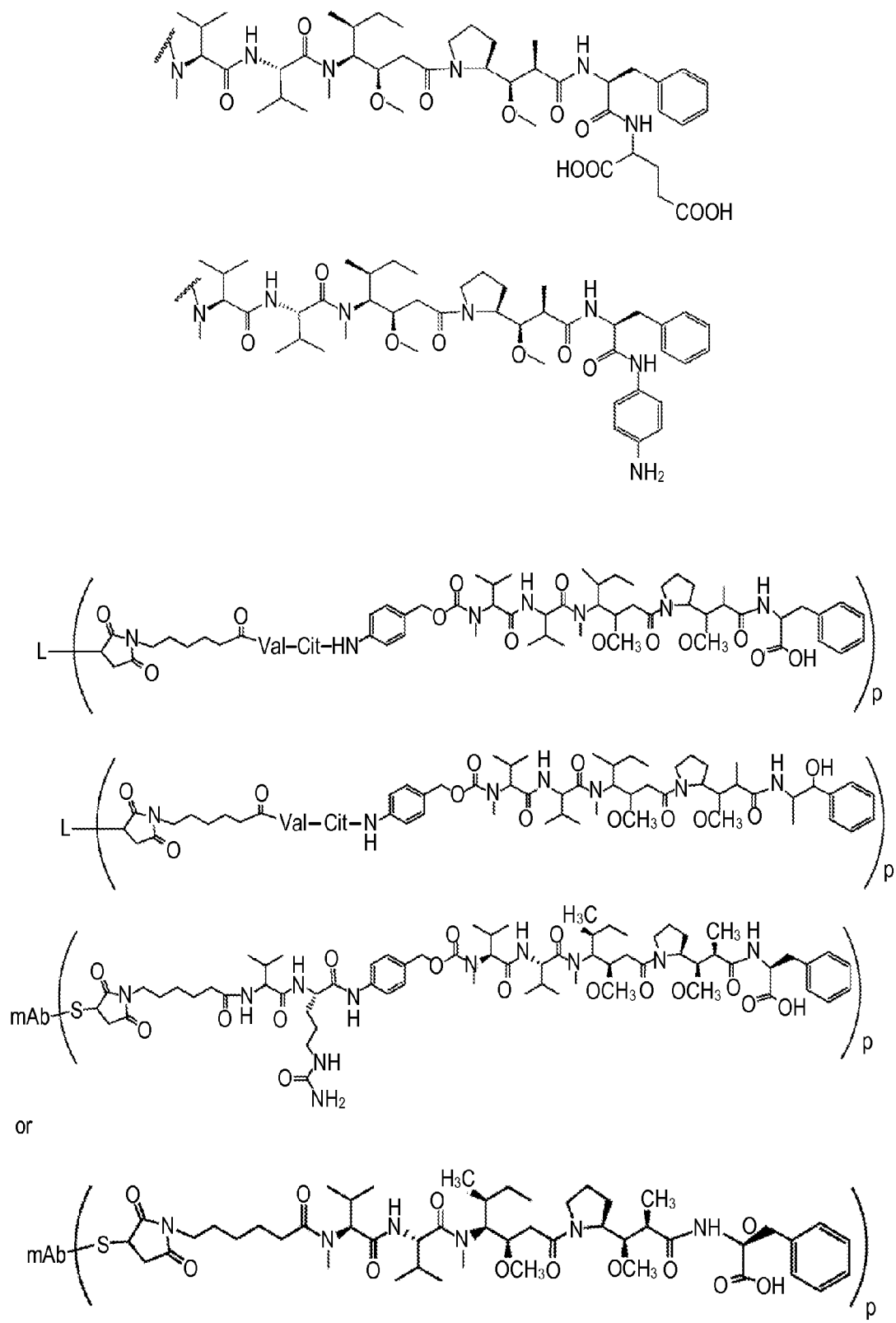
Figure 13:
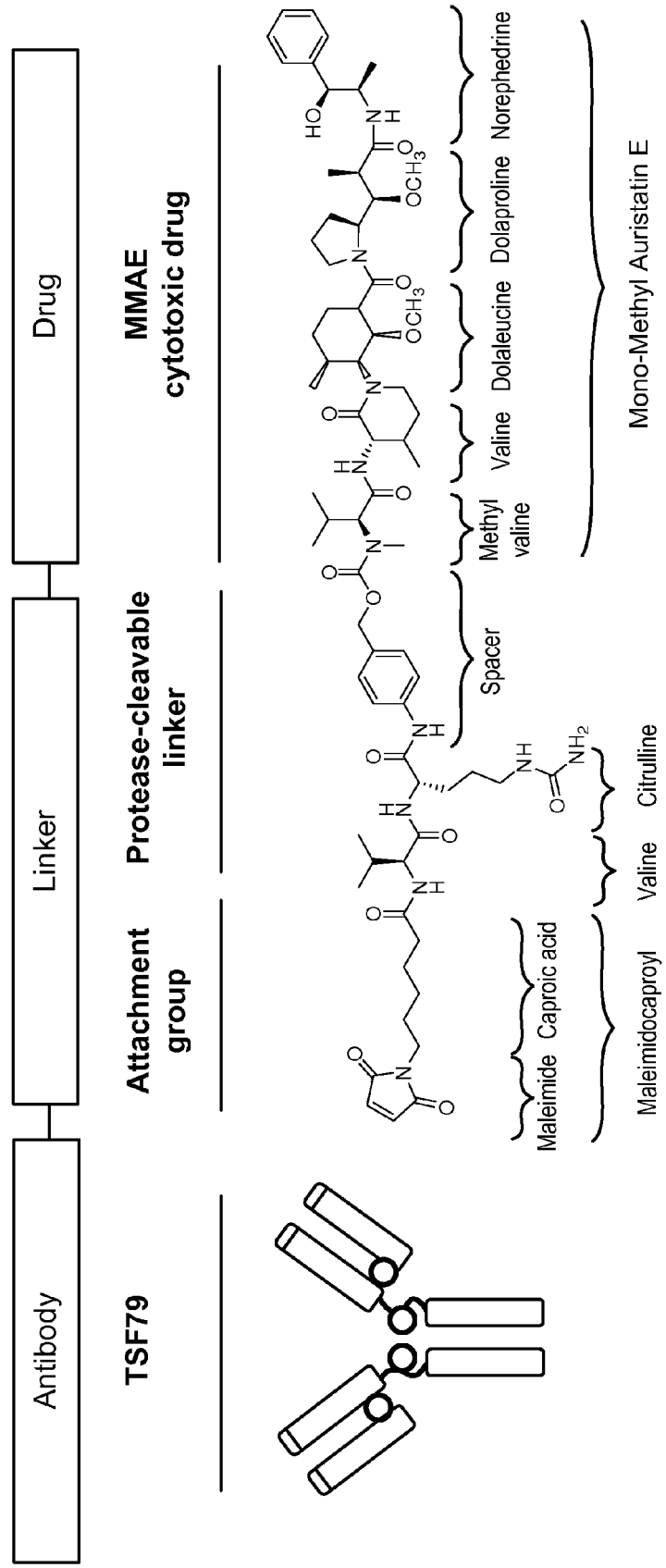
FIG. 13 depicts the structure of a preferred linker/drug combination. As will be appreciated by those in the art, the TSF79 (e.g. Ab79) antibody depicted herein can be switched to the AB19 antibody. Similarly, as discussed herein, any number of additional drug/linker combinations can be used, in addition to the auristatin E derivative shown herein.
Figure 14:
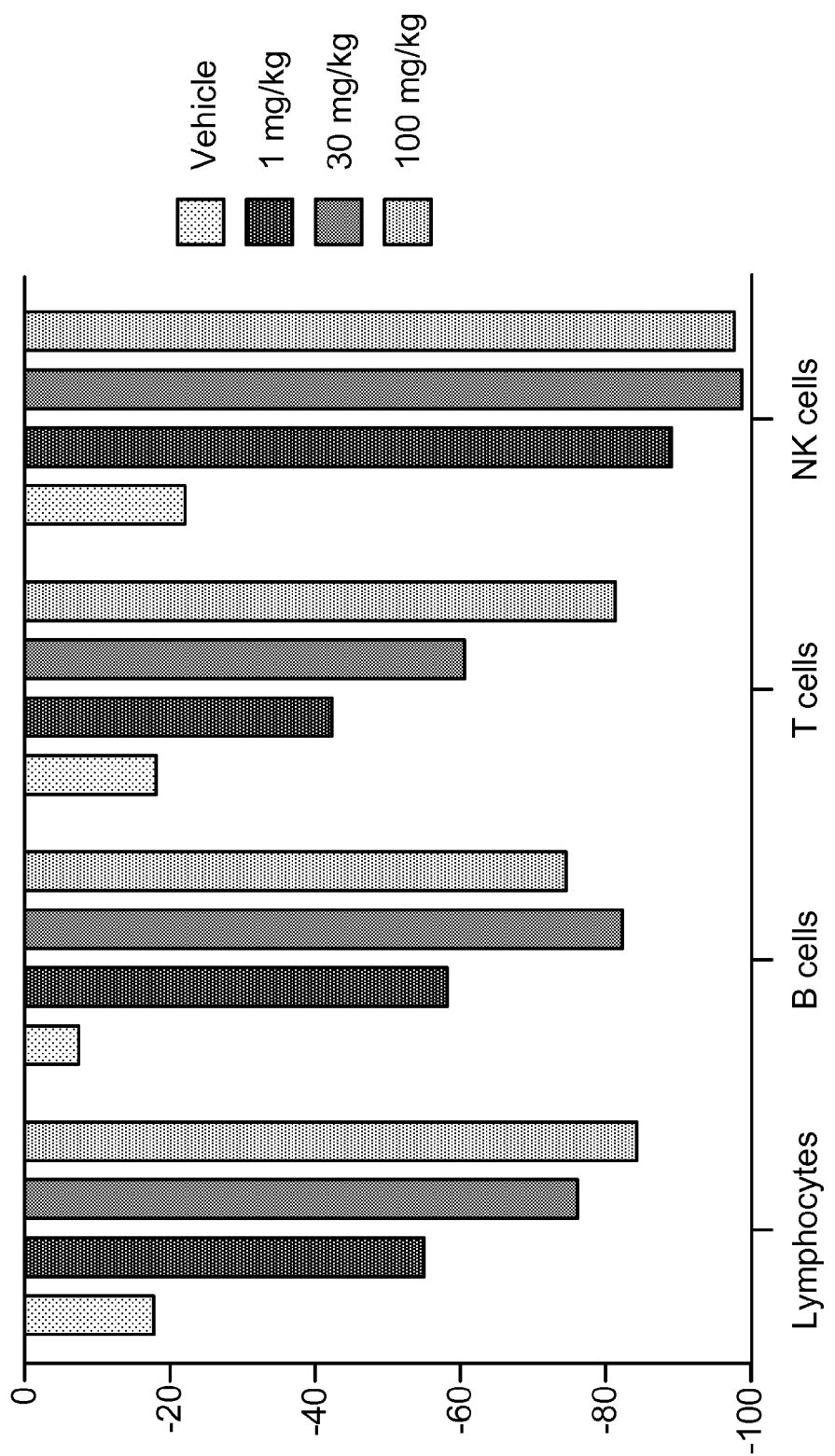
FIG. 14 depicts the percentage change in cell numbers in cyno monkeys at 24 hours after dosing.
Figure 15:
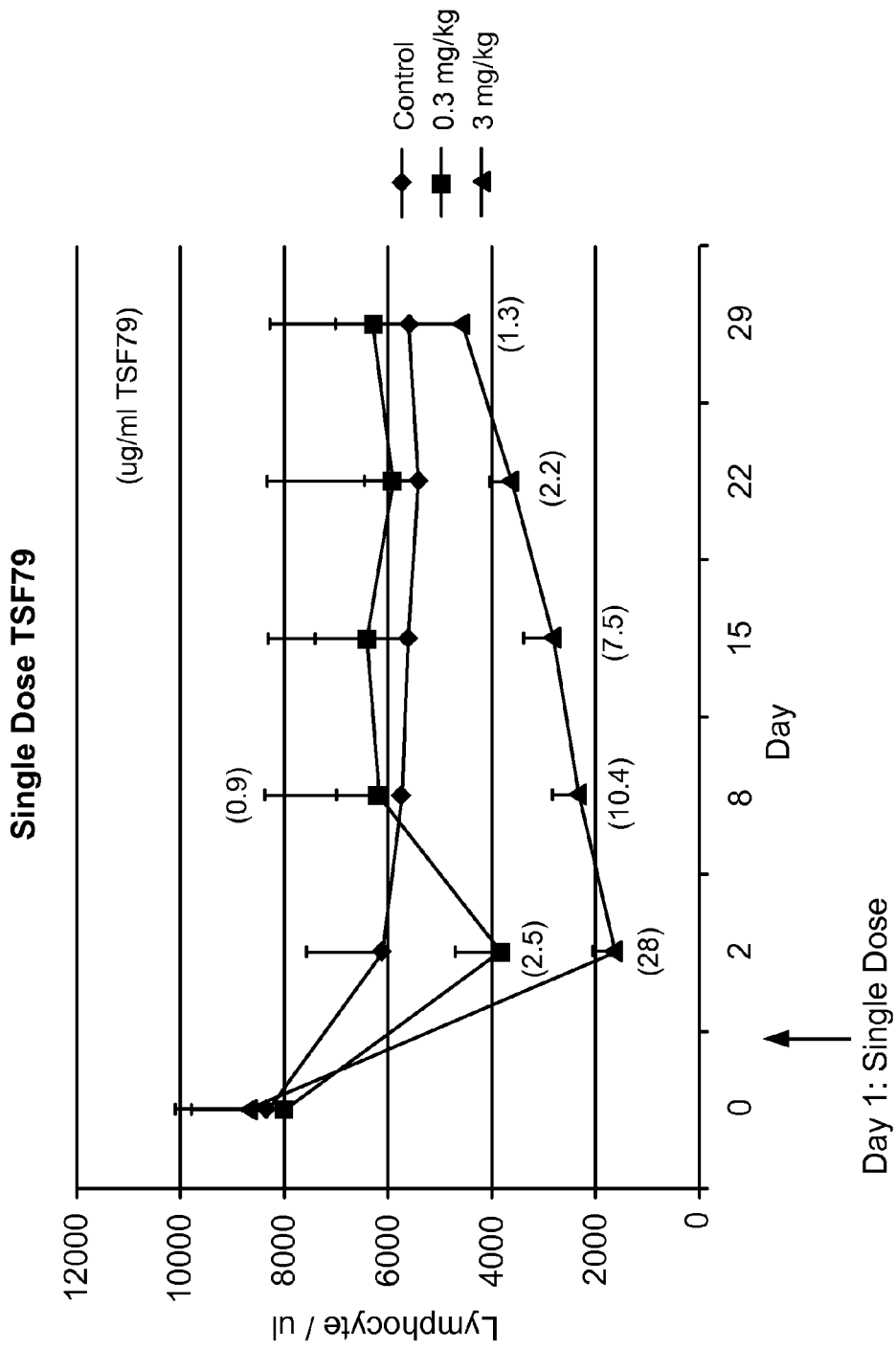
FIG. 15 shows the recovery of depletion after a single dose of Ab79.

An exemplary auristatin embodiment is MMAE (shown in FIG. 10 wherein the wavy line indicates the covalent attachment to a linker (L) of an antibody drug conjugate; see U.S. Pat. No. 6,884,869 expressly incorporated by reference in its entirety).

Another exemplary auristatin embodiment is MMAF, shown in FIG. 10 wherein the wavy line indicates the covalent attachment to a linker (L) of an antibody drug conjugate (US 2005/0238649, U.S. Pat. Nos. 5,767,237 and 6,124,431, expressly incorporated by reference in their entirety):

Additional exemplary embodiments comprising MMAE or MMAF and various linker components (described further herein) have the following structures and abbreviations (wherein Ab means antibody and p is 1 to about 8):

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin

In other embodiments, the ADC comprises an antibody of the invention conjugated to one or more calicheamicin molecules. For example, Mylotarg is the first commercial ADC drug and utilizes calicheamicin γ1 as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773,001, 5,767,285 and 5,877,296, all expressly incorporated by reference. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α2I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Duocarmycins

CC-1065 (see U.S. Pat. No. 4,169,888, incorporated by reference) and duocarmycins are members of a family of antitumor antibiotics utilized in ADCs. These antibiotics appear to work through sequence-selectively alkylating DNA at the N3 of adenine in the minor groove, which initiates a cascade of events that result in apoptosis.

Important members of the duocarmycins include duocarmycin A (U.S. Pat. No. 4,923,990, incorporated by reference) and duocarmycin SA (U.S. Pat. No. 5,101,038, incorporated by reference), and a large number of analogues as described in U.S. Pat. Nos. 7,517,903, 7,691,962, 5,101,038; 5,641,780; 5,187,186; 5,070,092; 5,070,092; 5,641,780; 5,101,038; 5,084,468, 5,475,092, 5,585,499, 5,846,545, WO2007/089149, WO2009/017394A1, 5,703,080, 6,989,452, 7,087,600, 7,129,261, 7,498,302, and 7,507,420, all of which are expressly incorporated by reference.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun 80: 49-57 can be used to incorporate Iodine-123. "Monoclonal Antibodies in Immunoscintigraphy" (Chatal, CRC Press 1989) describes other methods in detail.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined.

In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is 2, 3, 4, 5, 6, 7, or 8 or a fraction thereof.

The generation of Antibody-drug conjugate compounds can be accomplished by any technique known to the skilled artisan. Briefly, the Antibody-drug conjugate compounds can include an anti-CD38 antibody as the Antibody unit, a drug, and optionally a linker that joins the drug and the binding agent.

A number of different reactions are available for covalent attachment of drugs and/or linkers to binding agents. This is can be accomplished by reaction of the amino acid residues of the binding agent, for example, antibody molecule, including the amine groups of lysine, the free carboxylic acid groups of glutamic and aspartic acid, the sulfhydryl groups of cysteine and the various moieties of the aromatic amino acids. A commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule.

Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In some embodiments, an intermediate, which is the precursor of the linker, is reacted with the drug under appropriate conditions. In other embodiments, reactive groups are used on the drug and/or the intermediate. The product of the reaction between the drug and the intermediate, or the derivatized drug, is subsequently reacted with an anti-CD38 antibody of the invention under appropriate conditions.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug Linker Units Typically, the antibody-drug conjugate compounds comprise a Linker unit between the drug unit and the antibody unit. In some embodiments, the linker is cleavable under intracellular or extracellular conditions, such that cleavage of the linker releases the drug unit from the antibody in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in CD38-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: X)). Other examples of such linkers are described, e.g., in U.S. Pat. No. 6,214,345, incorporated herein by reference in its entirety and for all purposes.

In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See for example, WO 2007059404A2, WO06110476A2, WO05112919A2, WO2010/062171, WO09/017394, WO07/089149, WO 07/018431, WO04/043493 and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the anti-CD38 antibodies of the invention.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

Drug Loading

Drug loading is represented by p and is the average number of Drug moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, drug loading of from 1 to 4 is frequently useful, and from 1 to 2 is also useful. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

In vivo, the effect of a therapeutic composition of the anti-CD38 antibody of the invention can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). Efficacy can be measured using assays that measure inhibition of tumor formation, tumor regression or metastasis, and the like.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Antibody Compositions for In Vivo Administration

Formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to provide antibodies with other specifcities. Alternatively, or in addition, the composition may comprise a cytotoxic agent, cytokine, growth inhibitory agent and/or small molecule antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration should be sterile, or nearly so. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Administrative Modalities

The antibodies and chemotherapeutic agents of the invention are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Thus for B cell tumors, the subject may experience a decrease in the so-called B symptoms, i.e., night sweats, fever, weight loss, and/or urticaria. For pre-malignant conditions, therapy with an anti-CD38 therapeutic agent may block and/or prolong the time before development of a related malignant condition, for example, development of multiple myeloma in subjects suffering from monoclonal gammopathy of undetermined significance (MGUS).

An improvement in the disease may be characterized as a complete response. By "complete response" is intended an absence of clinically detectable disease with normalization of any previously abnormal radiographic studies, bone marrow, and cerebrospinal fluid (CSF) or abnormal monoclonal protein in the case of myeloma.

Such a response may persist for at least 4 to 8 weeks, or sometimes 6 to 8 weeks, following treatment according to the methods of the invention. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-CD38 antibodies used in the present invention depend on the disease or condition to be treated and may be determined by the persons skilled in the art.

An exemplary, non-limiting range for a therapeutically effective amount of an anti-CD38 antibody used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, he antibody is administered in a dose of 1 mg/kg or more, such as a dose of from 1 to 20 mg/kg, e.g. a dose of from 5 to 20 mg/kg, e.g. a dose of 8 mg/kg.

A medical professional having ordinary skill in the art may readily determine and prescribe the effective amount of the pharmaceutical composition required. For example, a physician or a veterinarian could start doses of the medicament employed in the pharmaceutical composition at levels lower than that required in order to achieve the desired therapeutic effect and gradually increase the dosage until the desired effect is achieved.

In one embodiment, the anti-CD38 antibody is administered by infusion in a weekly dosage of from 10 to 500 mg/kg such as of from 200 to 400 mg/kg Such administration may be repeated, e.g., 1 to 8 times, such as 3 to 5 times. The administration may be performed by continuous infusion over a period of from 2 to 24 hours, such as of from 2 to 12 hours.

In one embodiment, the anti-CD38 antibody is administered by slow continuous infusion over a long period, such as more than 24 hours, if required to reduce side effects including toxicity.

In one embodiment the anti-CD38 antibody is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-CD38 antibody.

In a further embodiment, the anti-CD38 antibody is administered once weekly for 2 to 12 weeks, such as for 3 to 10 weeks, such as for 4 to 8 weeks.

In one embodiment, the anti-CD38 antibody is administered by maintenance therapy, such as, e.g., once a week for a period of 6 months or more.

In one embodiment, the anti-CD38 antibody is administered by a regimen including one infusion of an anti-CD38 antibody followed by an infusion of an anti-CD38 antibody conjugated to a radioisotope. The regimen may be repeated, e.g., 7 to 9 days later.

As non-limiting examples, treatment according to the present invention may be provided as a daily dosage of an antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In some embodiments the anti-CD38 antibody molecule thereof is used in combination with one or more additional therapeutic agents, e.g. a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In some embodiments, the antibodies of the invention can be used prior to, concurrent with, or after treatment with Velcade® (bortezomib).

Diagnostic Uses

The anti-CD38 antibodies provided also find use in the in vitro or in vivo imaging of tumors or other disease states associated with CD38. In some embodiments, the antibodies described herein are used for both diagnosis and treatment, or for diagnosis alone. When anti-CD38 antibodies are used for both diagnosis and treatment, some embodiments rely on two different anti-CD38 antibodies to two different epitopes, such that the diagnostic antibody does not compete for binding with the therapeutic antibody, although in some cases the same antibody can be used for both. For example, in some instances, the Ab19 antibody is used diagnostically (generally labeled as discussed below) while Ab79 is used therapeutically, or vice versa. Thus included in the invention are compositions comprising a diagnostic antibody and a therapeutic antibody, and in some embodiments, the diagnostic antibody is labeled as described herein. In addition, the composition of therapeutic and diagnostic antibodies can also be co-administered with other drugs as outlined herein.

In many embodiments, a diagnostic antibody is labeled. By "labeled" herein is meant that the antibodies disclosed herein have one or more elements, isotopes, or chemical compounds attached to enable the detection in a screen or diagnostic procedure. In general, labels fall into several classes: a) immune labels, which may be an epitope incorporated as a fusion partner that is recognized by an antibody, b) isotopic labels, which may be radioactive or heavy isotopes, c) small molecule labels, which may include fluorescent and colorimetric dyes, or molecules such as biotin that enable other labeling methods, and d) labels such as particles (including bubbles for ultrasound labeling) or paramagnetic labels that allow body imagining. Labels may be incorporated into the antibodies at any position and may be incorporated in vitro or in vivo during protein expression, as is known in the art.

Diagnosis can be done either in vivo, by administration of a diagnostic antibody that allows whole body imaging as described below, or in vitro, on samples removed from a patient. "Sample" in this context includes any number of things, including, but not limited to, bodily fluids (including, but not limited to, blood, urine, serum, lymph, saliva, anal and vaginal secretions, perspiration and semen), as well as tissue samples such as result from biopsies of relevant tissues.

In some embodiments, in vivo imaging is done, including but not limited to ultrasound, CT scans, X-rays, MRI and PET scans, as well as optical techniques, such as those using optical labels for tumors near the surface of the body.

In vivo imaging of tumors associated with CD38 may be performed by any suitable technique. For example, $^{99}$Tc-labeling or labeling with another β-ray emitting isotope may be used to label anti-CD38 antibodies. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993).

In one embodiment, the present invention provides an in vivo imaging method wherein an anti-CD38 antibody is conjugated to a detection-promoting agent, the conjugated antibody is administered to a host, such as by injection into the bloodstream, and the presence and location of the labeled antibody in the host is assayed. Through this technique and any other diagnostic method provided herein, the present invention provides a method for screening for the presence of disease-related cells in a human patient or a biological sample taken from a human patient.

For diagnostic imaging, radioisotopes may be bound to an anti-CD38 antibody either directly, or indirectly by using an intermediary functional group. Useful intermediary functional groups include chelators, such as ethylenediaminetetraacetic acid and diethylenetriaminepentaacetic acid (see for instance U.S. Pat. No. 5,057,313). In such diagnostic assays involving radioisotope-conjugated anti-CD38 antibodies, the dosage of conjugated anti-CD38 antibody delivered to the patient typically is maintained at as low a level as possible through the choice of isotope for the best combination of minimum half-life, minimum retention in the body, and minimum quantity of isotope, which will permit detection and accurate measurement.

In addition to radioisotopes and radio-opaque agents, diagnostic methods may be performed using anti-CD38 antibodies that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in magnetic resonance imaging, and fluorescent compounds.

In order to load an anti-CD38 antibody with radioactive metals or paramagnetic ions, it may be necessary to react it with a reagent having a long tail to which are attached a multiplicity of chelating groups for binding the ions. Such a tail may be a polymer such as a polylysine, polysaccharide, or other derivatized or derivatizable chain having pendant groups to which can be bound chelating groups such as, e.g., porphyrins, polyamines, crown ethers, bisthiosemicarbazones, polyoximes, and like groups known to be useful for this purpose.

Chelates may be coupled to anti-CD38 antibodies using standard chemistries. A chelate is normally linked to an anti-CD38 antibody by a group that enables formation of a bond to the molecule with minimal loss of immunoreactivity and minimal aggregation and/or internal cross-linking.

Examples of potentially useful metal-chelate combinations include 2-benzyl-DTPA and its monomethyl and cyclohexyl analogs, used with diagnostic isotopes in the general energy range of 60 to 4,000 keV, such as $^{125}$I, $^{123}$I, $^{124}$I, $^{62}$Cu, $^{64}$Cu, $^{18}$F, $^{111}$In, $^{67}$Ga, $^{99}$Tc, $^{94}$Tc, $^{11}$C, $^{13}$N, $^{5}$O, and $^{76}$Br, for radio-imaging.

Labels include a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, or other γ-, β-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds.

These and similar chelates, when complexed with non-radioactive metals, such as manganese, iron, and gadolinium may be useful for MRI diagnostic methods in connection with anti-CD38 antibodies. Macrocyclic chelates such as NOTA, DOTA, and TETA are of use with a variety of metals and radiometals, most particularly with radionuclides of gallium, yttrium, and copper, respectively. Such metal-chelate complexes may be made very stable by tailoring the ring size to the metal of interest. Other ring-type chelates such as macrocyclic polyethers, which are of interest for stably binding nuclides, such as $^{223}$Ra may also be suitable in diagnostic methods.

Thus, the present invention provides diagnostic anti-CD38 antibody conjugates, wherein the anti-CD38 antibody conjugate is conjugated to a contrast agent (such as for magnetic resonance imaging, computed tomography, or ultrasound contrast-enhancing agent) or a radionuclide that may be, for example, a γ-, β-, α-, Auger electron-, or positron-emitting isotope.

Anti-CD38 antibodies may also be useful in, for example, detecting expression of an antigen of interest in specific cells, tissues, or serum. For diagnostic applications, the antibody typically will be labeled with a detectable moiety for in vitro assays. As will be appreciated by those in the art, there are a wide variety of suitable labels for use in in vitro testing. Suitable dyes for use in this aspect of the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals"; see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes (including Alexa, phycoerythin, bodipy, and others described in the 6th Edition of the Molecular Probes Handbook by Richard P. Haugland, hereby expressly incorporated by reference.

Stained tissues may then be assessed for radioactivity counting as an indicator of the amount of CD38-associated peptides in the tumor. The images obtained by the use of such techniques may be used to assess biodistribution of CD38 in a patient, mammal, or tissue, for example in the context of using CD38 as a biomarker for the presence of invasive cancer cells.

Articles of Manufacture

In other embodiments, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLES

The following examples are offered to illustrate, but not to limit the invention.

Example 1

Construction of Expression Vectors Comprising Polynucleotides Encoding Human, Cynomolgus Monkey, and Mouse CD38

To construct a vector expressing human CD38 (huCD38), a polynucleotide encoding huCD38 was isolated from cDNA obtained from Origene Technologies Trueclone® human. The isolated huCD38 was cloned into a stable expression vector (XOMA, Inc.) containing the neomycin resistance ($neo^R$) gene, which allowed for the selection of G418 (Geneticin)-resistant transfectants. The huCD38 gene present in the selected transfectants was sequenced to identify any sequence errors. Errors in the sequence that deviated from Genbank accession NM_001775 were corrected by PCR site-directed mutagenesis. The final vector DNA was confirmed by 5' sequencing.

To construct a vector expressing cynomolgus monkey CD38 (cyCD38), a polynucleotide encoding cyCD38 was isolated from DNA obtained from Biochain Institute's cDNA -monkey (cynomolgus)-normal spleen tissue. The isolated cyCD38 was cloned into a stable expression vector (XOMA, Inc.) containing the $neo^R$ gene, which allowed for the selection of G418 (Geneticin)-resistant transfectants. The cyCD38 gene present in the selected transfectants was sequenced to identify any sequence errors. Errors in the sequence that deviated from Genbank accession AY555148 were corrected by PCR sitedirected mutagenesis. The final vector DNA was confirmed by sequencing.

To construct a vector expressing mouse CD38 (moCD38), a polynucleotide encoding moCD38 was isolated from DNA obtained from Origene's TrueORF collection. The isolated moCD38 was cloned into a stable expression vector (XOMA, Inc.) containing the $neo^R$ gene, which allowed for the selection of G418 (Geneticin)-resistant transfectants. The moCD38 gene present in the selected transfectants was sequenced to identify any sequence errors. Errors in the sequence that deviated from Genbank accession NM_007646 were corrected by PCR site-directed mutagenesis. The final vector DNA was confirmed by sequencing.

Example 2

Development of CD38 Expressing Chinese Hamster Ovary (CHO) Cells

For development of CHO cells expressing huCD38, muCD38 and cyCD38, CHO cells were transfected with linearized DNA. After one week under selection, the cells were sorted by flow cytometry and the highest huCD38, muCD38 or cyCD38 expressing cells (top 15%) were plated in 96-well plates to generate single colonies. The remaining cells were also plated under selection to generate backup colonies. Approximately 12-14 days after plating, single colonies were identified and transferred to 96-deep-well plates. Clones were screened by FACS analysis after the second passage. Top producing clones were passaged and expanded to shake flasks. The top 2 clones were frozen and/or cultured for mycoplasmal AVA testing and scale-up.

To construct a luciferase reporter for disseminated xenograft models, a commercial vector containing the CMV promoter/luciferase gene/neomycin selectable marker (Promega, Madison, Wis.) was used to generate stable transfectant line in Daudi Burkitt's lymphoma cells.

Example 3

Phage Display Libraries and Screening of Agents that Bind CD38

Selection of target specific antibody from a phage display library was carried out according to methods described by Marks et al. (2004, Methods Mol. Biol. 248:161-76). Briefly, the phage display library was incubated with 100 pmols of biotinylated CD38 at room temperature for 1 hr and the complex formed was then captured using 100 μL, of Streptavidin bead suspension (DYNABEADS® M-280 Streptavidin, Invitrogen). Non-specific phages were removed by washing the beads with wash buffer (5% milk in PBS). Bound phages were eluted with 0.5 ml of 100 nM triethyleamine (TEA) and immediately neutralized by addition of an equal volume of 1M TRIS-CI, pH 7.4. The eluted phage pool was used to infect TG1 E. coli cells growing in logarithmic phase and phagemid was rescued as described in Marks et al., Id. Selection was repeated for a total of three rounds.

Alternatively, phage display libraries were panned against immobilized CD38 (R&D systems) to identify a panel of antibody fragments with the ability to bind CD38. Panning was carried out using standard protocols (see, e.g., Methods in Molecular Biology, vol. 178: Antibody Phage Display: Methods and Protocols Edited by: P.M. O'Brien and R. Aitken, Humana Press; "Panning of Antibody Phage-Display Libraries," Coomber, D. W. J., pp. 133-145, and "Selection of Antibodies Against Biotinylated Antigens," Chames et al., pp. 147-157). Briefly, three wells of a NUNC® MAXISORP plate were coated with 50 μL, of recombinant CD38 (R&D Systems) at a concentration of 10 μg/ml in PBS. After overnight incubation at 4° C., free binding sites were blocked with 5% milk in PBS for one hour at room temperature. Approximately 200 μL, of phage library in 5% milk/PBS was then added to the blocked wells and incubated at room temperature for approximately one to two hours. Wells were washed and bound phage was eluted using standard methods (see, e.g., Sam brook and Russell, Molecule Cloning: A Laboratory Manual, $3^{rd}$ Edition, Cold Spring Harbor Laboratory Press, 2001). Eluted phage was amplified via infecting *E. coli* TG 1 host cells in logarithmic growth phase. Infected TG 1 cells were recovered by centrifugation at 2,500 RPM for five minutes, plated onto 15 cm 2YT-ampicillin-2% glucose agar plates, and incubated at 30° C. overnight. The panning process was then repeated using the amplified phage. The cycle of panning, elution, and amplification was repeated for three rounds.

After panning completion, single colonies from the plated TG1 cells were used to inoculate media in 96-well plates. Microcultures were grown to an OD600 of 0.6, at which point expression of soluble scFv was induced by addition of 1 mM IPTG and overnight incubation in a shaker at 30° C. Bacteria were pelleted by centrifugation and periplasmic extract was used to test scFv binding to immobilized CD38 using a standard ELISA assay and a FACS-binding assay.

For FACS binding screen, CHO cells stably expressing CD38 were used to screen scFvs in periplasmic extract (PPE) for their ability to bind native, membrane bound CD38. Parental and CHO transfectants (Human CD38 or Cyno CD38 or Mouse CD38-expressing cell lines) were resuspended separately at $2\times10^6$ cells/ml in PBS (Life Technologies), 0.5% BSA (SigmaAldrich), and 0, 1% NaN3 (SigmaAldrich) (FACS buffer). Parental CHO cells not expressing CD38 were used as a negative control. Twenty five µL, aliquots of the cells were plated in Vbottomed 96-well plates (Costar Cat #3897) and 25 µL, of periplasmic extract containing myc-tagged scFv antibody fragment was added to the cells, then the mixture was incubated at 4° C. for 30 minutes. The cells were then washed twice after which the pellet was resuspended in 25 µL, of mouse anti c-myc (1/1000 in FACS buffer)(Roche) and again incubated at 4° C. for 30 minutes. The cells were then washed twice and resuspended in 25 µL, of 1/200 dilution anti-mouse IgG-PE in FACS buffer (Jackson labs) and again incubated at 4° C. for 30 minutes. The cells were then washed twice to remove excess unbound antibody and resuspended in 70 µL, FACS buffer and analysed on a BD FACScan®. The acquired data was evaluated using FlowJo software (TreeStar, Inc.). Positive samples were identified by comparing the median fluorescence intensity of the CD38 transfected CHO cell relative to the median fluorescence intensity of the parental CHO cell-line (CD38⁻).

Antibody clones that bound human CD38 were sequenced to identify unique clones. The unique scFV clones were then ranked based on off-rates determined by Biacore® analysis. 200 RU to 500 RU of human recombinant CD38 (R&D Systems' cat #2404-AC or equivalent) were immobilized by standard amine coupling chemistry (Biacore®) to a CM5 or equivalent chip. A reference spot was also prepared which was activated and then blocked without the immobilization of the protein. This was done by diluting the antigen to 1-3 µg/ml in acetate buffer, pH 5.0, and injecting over the activated surface until required level was immobilized (3-5) minutes. The surface was then blocked with ethanolamine. Periplasmic extracts were diluted one-to-one with the assay running buffer 10 mM HEPES, 150 mM NaCl, 3 mM EDTA (ethylenediaminetetraacetic acid), and 0.05% polysorbate 20 at pH 7.4 with 2 mg/mL BSA (bovine serum albumin)). The diluted periplasmic extract was injected over the surface plasmon resonance (SPR) surfaces at 30 minute for 300 seconds with an additional 900 seconds of dissociation time monitored. Regeneration was with a single 8-second injection of 100 mM HCl. Data from the reference sp,pts were subtracted from the data from the active surface, then dissociation curves were fit using the 1:1 dissociation model in the Biacore® T100 software.

Top-ranking scFV clones were converted to IgG1 antibodies. The FACS binding screen was repeated on the IgG1 reformatted clones using parental CHO cells and CHO cells expressing human, murine and cynomolgus CD38 to ensure binding properties were retained and to assess species cross-reactivity. FACS characterization of IgG-reformatted clones was conducted as described above, but the steps consisting of the addition of anti-c-myc antibody and anti-mouse IgG-PE were replaced by a single step in which binding of full-length human IgG was detected by the addition of phycoerythrin conjugated anti-human IgG (Jackson Labs).

Example 4

In Vitro Cell-Based Assays of IgG-Reformatted Clones

About 150 clones were reformatted as human IgG1 antibodies and five (Ab19, Ab43, Ab72, Ab79, and Ab110) were fully evaluated using a panel of assays, as described below. Performance of IgG-reformatted clones in both in vitro and in vivo assays was compared to two antibodies, BMTK4-1 (also called benchmark-1, BM-1, or BMTK-1) (SEQ ID NOs:24 and 25; heavy and light chain variable regions) and BMTK4-2 (also called benchmark-2, BM-2, or BMTK-2) (SEQ ID NOs: 26 and 27; heavy and light chain variable regions), the amino acid sequences of which were derived from the sequences of known anti-CD38 antibodies daratumumab (also called HuMax-CD38, disclosed in International Publication No. WO 06/099875) and SAR650984 (disclosed in International Publication No. WO 08/047242), respectively. Palivizumab (SYNAGIS®) (MedImmune), a clinically approved antibody that recognizes respiratory syncytial virus served as a negative control for CD38 binding.

Example 5

Detection of Ab79 Binding by Immunofluorescence

Figure 4:
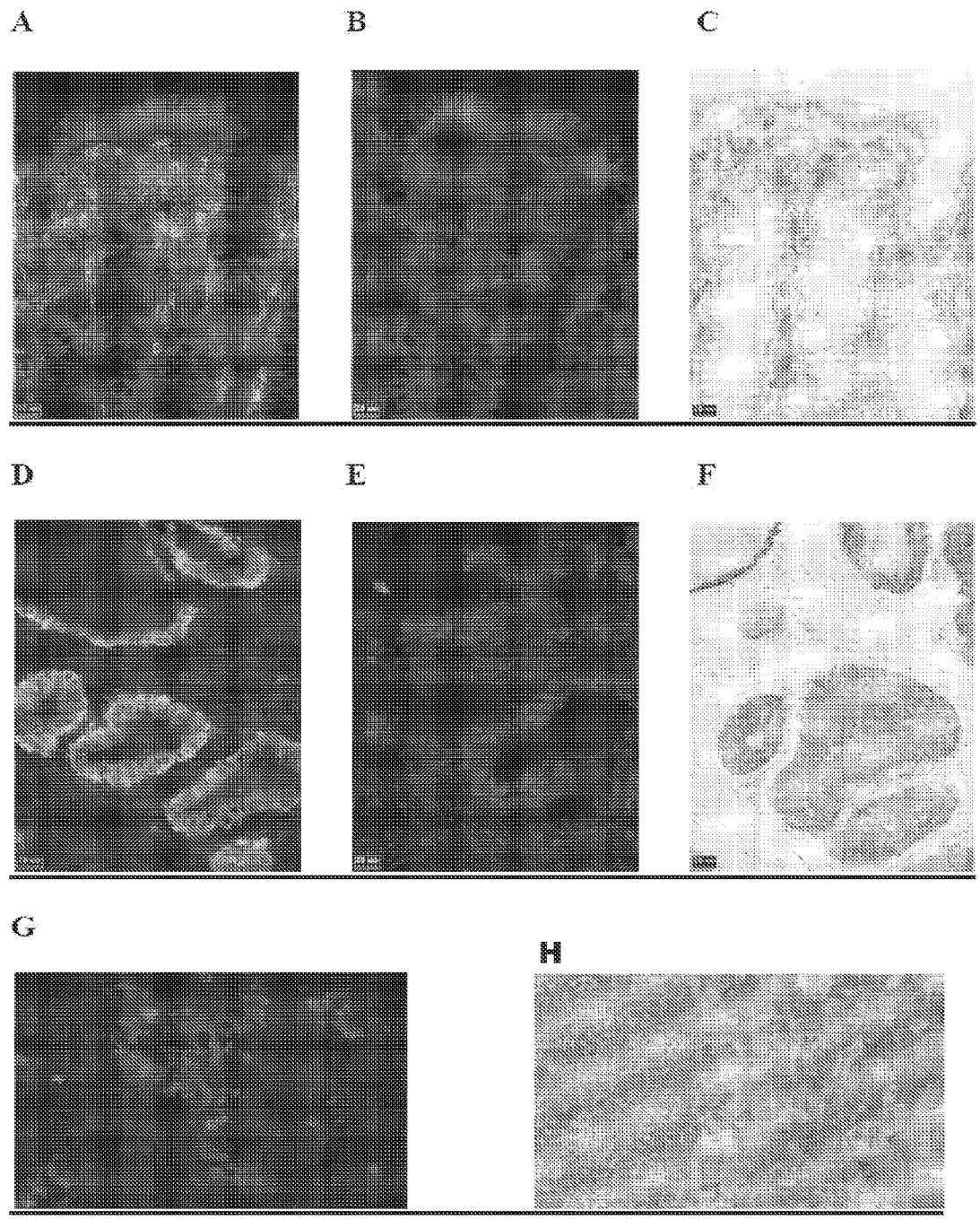
FIG. 4 shows detection of Ab79 binding to normal tissues by immunofluorescence. (A) normal human colon stained with Ab79 (B) normal human colon stained with irrelevant control antibody Palivizumab (C) light microscopy of normal human colon counterstained with hematoxylin (D) normal human prostate stained with Ab79 (E) normal human prostate stained with irrelevant control antibody Palivizumab (F) light microscopy of normal human prostate counterstained with hematoxylin (G) normal human lymph node stained with Ab79 (H) light microscopy of normal human lymph node counterstained with hematoxylin

Alexa Fluor®-488 dye labeled Ab79 was applied to frozen sections of normal human colorectal tissue, prostate, and lymph. Alexa Fluor®-488 dye labeled Palivizumab (Synagis®) served as a negative staining control. The resulting immunofluorescent images are shown in FIG. 4. The staining pattern observed for Ab79 was identical to that seen with a commercially available polyclonal anti-CD38 antibody on normal human colorectal tissue, prostate and lymph node (data not shown).

Alexa Fluor®-488 dye labeled Ab79 was also applied to normal and multiple myeloma bone marrow specimens (FIG. 5). Whereas Ab79 bound to 10% of the cells from normal bone marrow, >90% of the multiple myeloma bone marrow cells, in 4 out of 4 tested samples, showed Ab79 binding.

The ability of Ab79 to bind to a number of cell lines (MOLP-8, DAUDI, RPMI, and MCF7) was also examined MOLP-8 (human multiple myeloma), DAUDI (lymphoblast derived from a patient with Burkitt's lymphoma), and RPMI (cell line established from patient with chronic myelogenesis leukemia) cells all showed binding by Ab79. The breast cancer line, MCF7, appeared largely negative for Ab79 binding (FIG. 6).

The Alexa Fluor® 488-conjugated antibodies were stained on 8 µm cryostat frozen sections, which were fixed in an ethanol/acetone mixture for 5 min followed by incubation with the antibodies for 1 hour at room temperature in a humidity-controlled chamber. The sections were then washed, a DAPI containing mountant (Vector Laboratories, cat #H1500) was added, and a coverslip was applied.

Example 6

Evaluation of Ab79 Expression on Multiple Myeloma (MM) and Chronic Lymphocytic Leukemia (CLL)

Figure 7A:
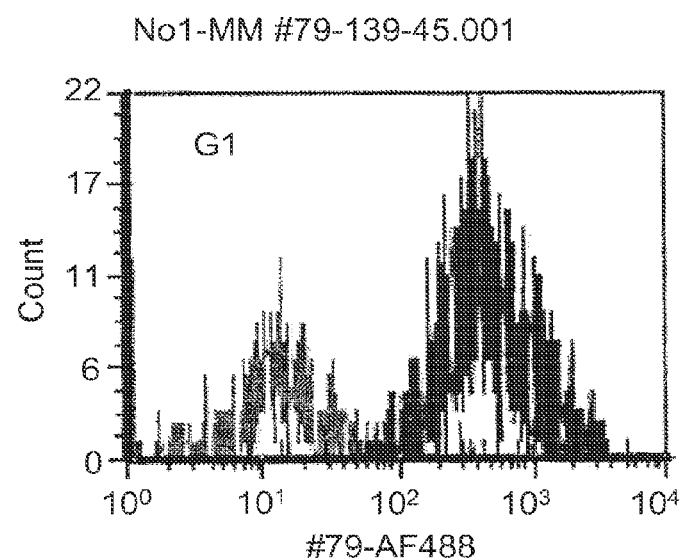
FIG. 7 shows FACS analysis of Ab79 expression on cells derived from the bone marrow of a Multiple Myeloma patient (A) and PBMCs from a patient with Chronic Lymphocytic Leukemia (gated on CD5$^+$cells) (B).
Figure 7B:
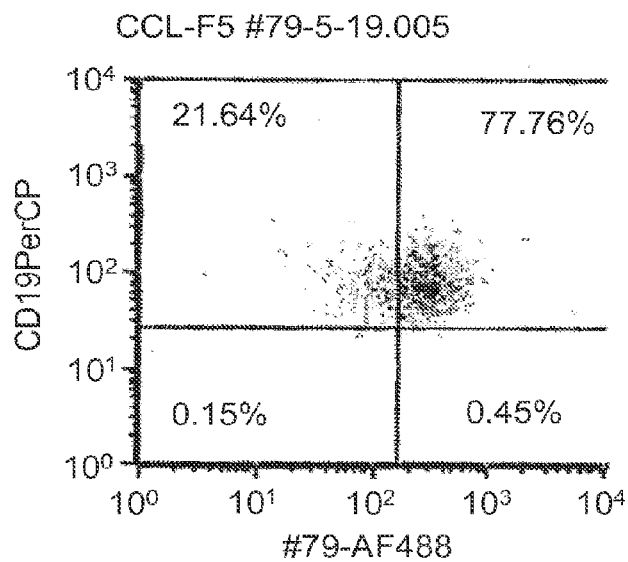

Ab79 binding to bone marrow samples from multiple myeloma patients was analyzed by flow cytometry either after enrichment for CD138$^+$ cells or by gating on CD138$^+$ CD45$^{-lo}$ cells (FIG. 7A). Ab79 was found to be expressed on >95% of cells from four out of six multiple myeloma samples. The binding pattern of Ab79 appeared largely similar to that of an anti-CD38 antibody used in clinical laboratories. Further, Ab79 bound cells from patients with chronic lymphocytic leukemia (FIG. 7B).

In order to measure Ab79 binding to MM and CLL by FACS patient samples were processed within 24 hours. Peripheral blood mononuclear cells were isolated by Ficoll-Paque™ (GE Healthcare) according to the manufacturer's instructions. Expression analysis was performed using the following panels of antibodies with clones in parentheses. MM panel: Ab79-Alexa Fluor®-488, CD45-PerCP(2D1), CD138-APC (MI15). CLL panel: Ab79-Alexa Fluor®-488; CD5-PE (UCHT2), CD45-PerCP(2D1), CD19-APC (SJ25C1). 5 µL of the PE, PerCP, or APC labeled antibody or 10 µL of Alexa Fluor®-488 labeled antibody or isotype control was added to each well or tube containing either 100 µL of 0.2×106 PBMCs or CD138 enriched cells from bone marrow aspirate. samples were incubated for 30 mins at room temperature following which red blood cells were lysed using BD Pharmlyse, according to the manufacturer's instructions. All samples were washed three times in FACS buffer. Samples were fixed in 1% paraformaldehyde and analyzed on a BD FACSCanto™ II or BD FACSCaliber™.

Example 7

Anti-CD38 induced CDC assays

Cynomolgus cross-reactive clones were tested for the ability to induce complement-dependent cytotoxicity (CDC). MOLP-8 cells were plated at a density of 10,000 cells per well in a black 96-well flat-bottom tissue culture plate in 50 µL of complete media (RPMI supplemetned with 10% fetal bovine serum). 50 µL of 2× anti-CD38 antibody, control IgG antibody, or media alone was added to each well and left to incubate at room temperature for 10 min. Varying amounts (2-15 µL) of purified rabbit complement (cat #CL 3441 Cedarlane Laboratories, Canada), depending upon the cell line was added to each well except control wells. After one hour incubation at 37° C., plates were brought to room temperature, 100 µL of cell titer CytoTox Glo™ reagent (Promega G7571/G7573) was added per well, the plate shaken for 5 to 7 min and luminescence read on an EnVision® (Perkin Elmer) luminescence plate reader. Conditions tested: cells alone; cells+complement; cells+IgG control+complement; cells+antibody+complement. % CDC was calculated using the following equation:

$$100-(RLU_T/RLU_C \times 100),$$

where $RLU_T$ is the relative luminescence units of the test sample and $RLU_C$ is the relative luminescence units of the sample with complement alone. Statistical analysis was performed using PRISM software. $EC_{50}$ values, as determined from plots of % CDC versus antibody concentration, are shown in Table 1.

Example 8

Anti-CD38 Induced ADCC Assays

Antibody-dependent cell-mediated cytotoxicity (ADCC) was assessed using Daudi, MOLP-8, and RPMI-8226 cell lines as target cells. PBMCs were isolated as effector cells by Ficoll-Plaque™ separation from buffy coat or LRS which were obtained from the Stanford Blood Center (Palo Alto, Calif.). Specimens were diluted 1:3 with 2% FBS in PBS. 15 mL of Ficoll-Plaque™ (GE Healthcare) was gently layered under 35 mL of diluted specimen and centrifuged at 1800 rpm (brake off) for 25 min. The cloudy interphase containing PBMCs was collected, washed 3 times in 2% FBS in PBS and frozen aliquots of 50×106 cells/mL per aliquot in 10% DMSO/FBS. Frozen aliquots of PBMCs were thawed and cultured overnight in 10% FBS/RPMI+5 µg/mL recombinant human IL2 (R & D systems #202-IL) at 2×106 per mL, when needed.

For the ADCC assay, all steps were performed in complete media. 5000 target cells were plated per well in a 96-well plate in 50 µL of 3× anti-CD38, control IgG, or media alone was added followed by 50 µL of human effector PBMCs at a ration of between 1:25 to 1:50 target:effector (T:E) cells. Plates were briefly centrifuged for ~30 seconds at 800 rpm to bring all cells into close proximity. After 4 hrs at 37° C., plates were centrifuged at 1100 rpm for 5 min and 100 µL supernatant transferred to a white plate. 100 µL CytoTox Glo™ reagent (Promega cat # G9292) was added to the supernatant and plates were left to shake for 20-30 mins at RT. Luminescence was read on an EnVision® (Perkin Elmer) luminescence plate reader and percent specific lysis was calculated using the following equation:

$$(RLU_T/RLU_{E/T})/(RLU_L/RLU_{E/T}) \times 100$$

where $RLU_T$ is the relative luminescence units of the test sample and $RLU_{E/T}$ is the relative luminescence units of the sample containing target cells and effector cells alone, and $RLU_L$ is the relative luminescence units for cells lysed with Triton X-100. Statistical analysis was performed using PRISM software. $EC_{50}$ values, as determined from plots of % specific lysis versus antibody concentration, are shown in Table 1.

TABLE 1

CDC, ADCC, and Agonist Activity for IgG-Refomatted Antibodies

| Antibody | CDC EC50 nM (MOLP-8) | ADCC EC50 nM (DAUDI) | ADCC EC50 nM (MOLP-8) | ADCC EC50 nM (RPMI-8226) | Apoptosis EC50 nM (DAUDI) |
|---|---|---|---|---|---|
| BM-1 | 0.48 ± 0.16 | 0.03 ± 0.02 | 0.036 ± 0.013 | 0.13 ± 0.03 | 0.057 |
| BM-2 | 0.65 ± 0.18 | 0.04 ± 0.02 | 0.024 ± 0.005 | 0.15 ± 0.04 | 0.062 |
| Ab19 | 0.98 ± 0.26 | 0.08 ± 0.03 | 0.038 ± 0.008 | 0.46 ± 0.15 | 0.032 |
| Ab43 | 2.2 | 0.12 ± 0.09 | 0.027 ± 0.018 | 3.84 ± 1.34 | 1.56 |

TABLE 1-continued

CDC, ADCC, and Agonist Activity for IgG-Refomatted Antibodies

| Antibody | CDC EC50 nM (MOLP-8) | ADCC EC50 nM (DAUDI) | ADCC EC50 nM (MOLP-8) | ADCC EC50 nM (RPMI-8226) | Apoptosis EC50 nM (DAUDI) |
|---|---|---|---|---|---|
| Ab72 | 0.66 ± 0.49 | 0.14 ± 0.12 | 0.193 ± 0.037 | 2.35 ± 0.99 | 0.35 |
| Ab79 | 1.1 ± 0.39 | 0.03 ± 0.02 | 0.047 ± 0.012 | 0.46 ± 0.19 | 0.048 |
| Ab110 | 1.99 ± 0.71 | 0.24 ± 0.17 | 0.874 ± 0.804 | 2.98 ± 0.91 | 0.40 |
| Ab164 | 2.00 ± 0.83 | ND | 0.165 ± 0.154 | 1.2 ± 0.24 | 0.31 |

Example 9

Affinity Determination by FACS

MOLP-8 cells expressing CD38 were suspended in 1% FBS buffer at a viable cell concentration of approximately 2 million cells/mL. mAbs to be tested were serially diluted (2-fold) across wells over two 96-well plates in 1× PBS. The last well of each titration contained buffer only. Additional PBS and cell suspensions were added to each well so that the final volume was 300~L/well and each well contained approximately 100,000 cells. The mAbs are listed below with the corresponding final mAb binding site concentration (2× molecular concentration) range used for the titrations:

Benchmark 1, [mAb]bindingsite=50.8 nM-49.7 pM
Benchmark 2, [mAb]bindingsi,e=49.5 nM-48.3 pM
Ab 43, [mAb]binding site=49.3 nM-48.2 pM
Ab 110, [mAb]bindingsite=204 nM-49.9 pM
Ab 79, [mAb]binding Site=103 nM-25.3 pM
Ab 72, [mAb]binding Site=103 nM-25.2 pM
Ab 19, [mAb]bindingsite=100 nM-12.2 pM •

The plates were placed into a plate shaker for 5 hours at 4° C., after which the plates were washed 3 times at 4° C. with 1×PBS. 200 μl of 99 nM Cγ5 goat anti-human IgG Fc specific polyclonal antibody (Jackson ImmunoResearch Laboratories, #109-175-008) was then added to each well, and the plates were shaken for 30 minutes at 4° C. The plates were again washed 2× at 4° C. with 1×PBS, then a FACSCanto™ II HTS flow cytometer was used to record the mean fluorescence intensity (MFI) of 5000 events for each well containing a unique mAb binding site concentration. A plot of the Mean Fluorescence Intensity as a function of the antibody binding site concentration was fit nonlinearly with Scientist 3.0 software using the equation below to estimate KD:

$$F = p[(KD+LT+n(M)) - \{(KD+LT+n(M))2 - 4n(M)(LT)\}1/2]/2 + B$$

where F (mean fluorescence intensity), LT (total mAb binding site concentration), p (proportionality constant that relates arbitrary fluorescence units to bound mAb), M (cellular concentration in molarity; 0.553 fM based on 100,000 cells in 300 μl), n (number of receptors per cell), B (background signal), and KD=equilibrium dissociation constant.

For each antibody titration curve, an estimate for KD was obtained as P, n, B, and KD were floated freely in the nonlinear analysis. For a detailed derivation of the above equation, see Drake and Klakamp (2007), "A rigorous multiple independent binding site model for determining cell-based equilibrium dissociation constants," J. Immunol. Methods 318: 157-62, which is incorporated by reference herein. Table 3 lists the resulting KD's for all antibodies in order of decreasing affinity along with the 95% confidence interval of each fit in parentheses. The antibody binding site concentration (2× the molecular concentration) was used for the nonlinear curve-fitting.

Example 10

Affinity determination by Biacore®

The affinity of IgG antibodies to soluble CD38 ectodomain (ECD) was determined by surface plasmon resonance (SPR) analysis on a Biacore™ A100 at 22° C. Goat anti-human IgG polyclonal antibody (Caltag H10500) was immobilized to a CM5 biosensor chip using standard amine coupling to spots 1, 2, 4, and 5 within all four flow cells of the chip Immobilization levels on each spot ranged from 5865 RU to 6899 RU. Human CD38 was obtained from R&D Systems (Cat #2404-AC, Lot # PEH020812A). The stock concentration for CD38 was determined using methods detailed in Pace et al. (1995) "How to measure and predict molar absorption coefficient of a protein" Protein Science 4(11):2411-23 and Pace and Grimsley (2004) "Spectrophotometric determination of protein concentration," in Current Protocols in Protein Science, Chapter 3: Unit 3.1, the teaching of each reference being incorporated by reference herein.

Running buffer was prepared by degassing HEPES-buffered saline, 0.005% polysorbate 20, and adding filtered BSA to a final concentration of 100 μg/mL. All eight purified mAbs were diluted to approximately 2 μg/mL with running buffer. Preliminary experiments estimated the amount of each mAb to be captured in order to maintain a surface capacity ($R_{max}$) no greater than ~100 RU. For each mAb capture/antigen injection cycle, a mAb was captured over spots 1 and 5 within each flow cell with juxtaposed spots 2 and 4 serving as the respective reference surfaces. Each diluted mAb was captured for 1 minute at a flow rate of 10 μL/min followed by three minutes of flowing running buffer for surface stabilization. HuCD38 was injected over all four flow cells for 120 seconds at 30 μL/min over a concentration range of 193.7 nM-3.0 nM (2× serial dilution) followed by a 15 minute dissociation phase. The samples were all prepared in the running buffer and were randomly injected in triplicate with seven buffer injections interspersed for double referencing. The surfaces were regenerated with two 20 second pulses of 10 mM glycine, pH 1.7.

All sensorgram data were processed with Scrubber 2.0c software and globally fit to a 1:1 interaction model in Scrubber 2.0c. The resulting binding constants are shown in Table 2.

TABLE 2

| Antibody | FACS KD (nM) MOLP-8 | FACS KD (pM) RPMI-8226 | Biacore Ka (M-1s-1) | Biacore Kd (s-1) | Biacore KD (nM) |
|---|---|---|---|---|---|
| BM-1 | 1.1 (0.9) | 802 | $4.49 \times 10^4$ | $2.46 \times 10^{-3}$ | 54.8 |
| BM-2 | 1.6 (0.6) | 428 | $4.24 \times 10^5$ | $2.27 \times 10^{-3}$ | 5.4 |
| Ab19 | 0.4 (0.3) | — | $1.54 \times 10^5$ | $8.10 \times 10^{-4}$ | 5.3 |
| Ab79 | 1.2 (1.1) | 508 | $1.22 \times 10^5$ | $6.75 \times 10^{-4}$ | 5.5 |
| Ab72 | 0.6 (0.4) | — | $1.44 \times 10^4$ | $1.82 \times 10^{-3}$ | 126 |

TABLE 2-continued

| Antibody | FACS KD (nM) MOLP-8 | FACS KD (pM) RPMI-8226 | Biacore Ka (M-1s-1) | Biacore Kd (s-1) | Biacore KD (nM) |
|---|---|---|---|---|---|
| Ab110 | 1.0 (0.1) | — | $1.22 \times 10^5$ | $1.71 \times 10^{-1}$ | 1400 |
| Ab43 | 1.1 (0.3) | — | $2.72 \times 10^5$ | $1.46 \times 10^{-1}$ | 537 |
| Ab164 | 1.4 (0.7) | — | $1.99 \times 10^5$ | $7.15 \times 10^{-2}$ | 359 |

Example 11

Immunofluorescence Internalization Assays

Immunofluorescence techniques were used to evaluate the internalization of anti-CD38 antibodies into MOLP-8 cells. MOLP-8 cells were collected and $5 \times 10^6$ cells were stained for 10 min at 4° C. in RPMI-1640 with 1 ng of each anti-CD38 antibody directly conjugated to Alexa Fluor® 488. The cells were washed in PBS containing 1% BSA, and $1 \times 10^6$ cells were incubated for 3 or 6 hours at 4° C. or 37° C. Surface staining was quenched for 30 min at 4° C. using 2 µg of rabbit anti-Alexa Fluor®-488 antibody (Invitrogen). The cells were washed and fixed in PBS with 1% PFA, transfered to a Microtest 96-well plate (BD Biosciences), and either evaluated by flow cytometry using a FACSCanto™ II (BD Biosciences) flow cytometer or imaged using an ImageXpress® Micro (Molecular Devices) at 20× magnification.

Example 12

Epitope Binning by Biacore®

Biacore® A100 instrumentation was used to bi~ the two benchmark antibodies as well as Ab 19 and Ab 79. The antibodies were first immobilized at high and low densities on a CMS chip using NHS/EDC coupling chemistry. For each cycle of the epitope binning experiment, CD38 was first injected over these surfaces. Analogous to a sandwich assay in an ELISA format, a unique antibody (taken from the set of immobilized antibodies) was then injected over surfaces containing CD38/antibody complexes. Surfaces were regenerated using pulses of phosphoric acid at the end of each cycle. Data was collected at 22° C. using HBS-P (10 mM 10 HEPES pH 7.4, 150 mM NaCl, 0.005%) P-20) supplemented with BSA. The resulting sensorgrams were processed using the "Epitope Mapping" module in the Biacore® A100 Evaluation software package as well as a trial version of Scrubber for A100 data sets. Replicate data was used to generate a binary 4×4 matrix for the above 4 mAbs from two separate experiments, as shown in Table 3.

TABLE 3

|  | Ab79 | BM1 | Ab19 | BM2 |
|---|---|---|---|---|
| Ab79 | 0 | 0 | 1 | 1 |
| BM1 | 0 | 0 | 1 | 0 |
| Ab19 | 1 | 1 | 0 | 0 |
| BM2 | 1 | 0 | 0 | 0 |

Example 13

In Vivo Analysis

Figure 8:
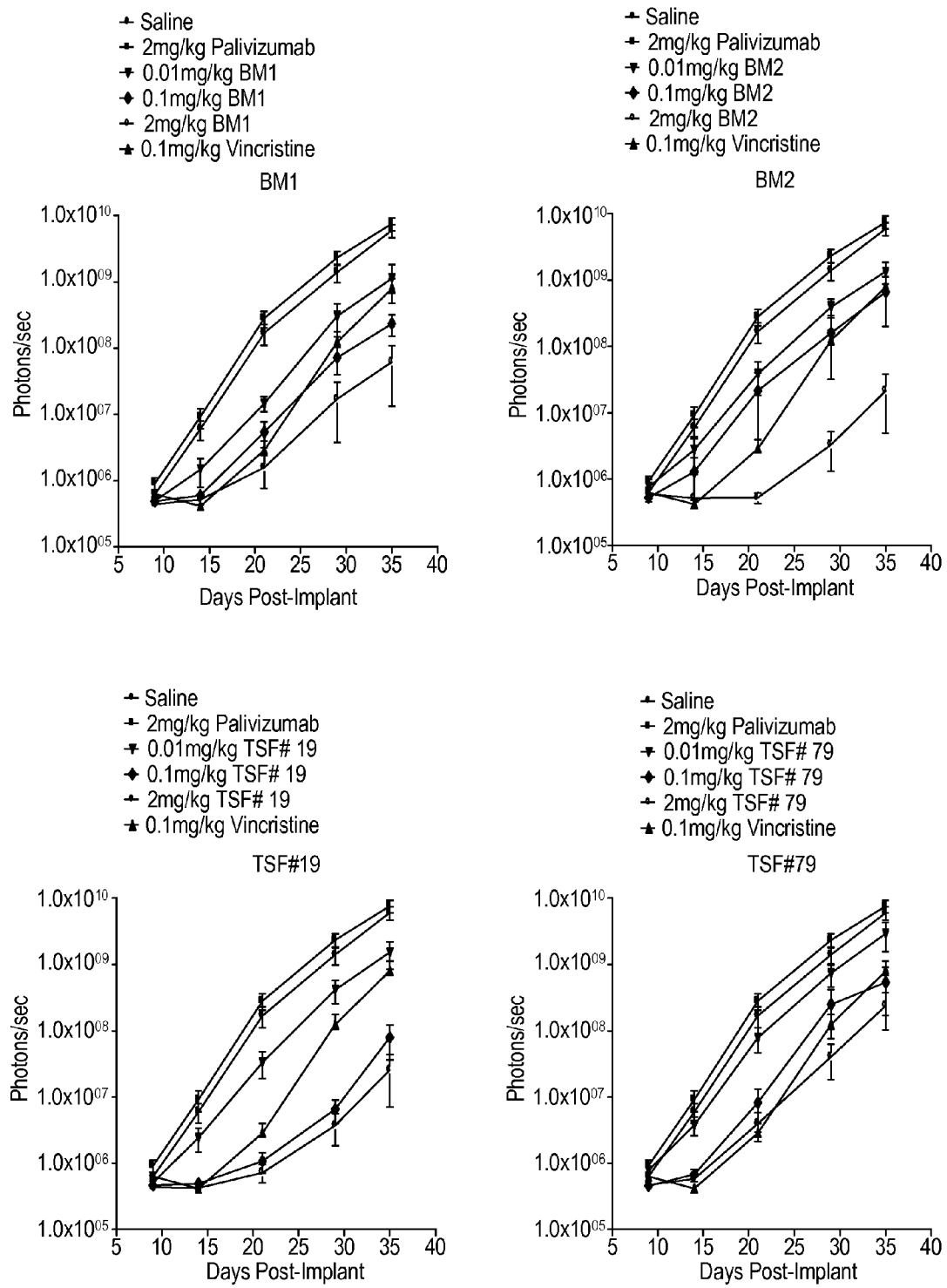
FIG. 8 depicts an in vivo dose response study comparing Ab19, Ab79, and benchmark antibodies BM1 and BM2.

The in vivo efficacy of Ab19 and Ab79 was tested in a disseminated Daudi-luciferase model of human lymphoma. 6-8 week old female CB.17 SCID mice from Taconic Laboratories were injected intravenously with $1 \times 10^6$ Daudi-Luc tumor cells. At study day 7, mice were treated intraperitoneally with: palivizumab, Ab 79, Ab19, Benchmark 1, and Benchmark 2. Bioluminescent imaging was performed weekly starting from day 21 using an IVIS Xenogen system (Caliper Life Sciences) to monitor tumor burden. For imaging, animals were injected IP with luciferase substrate (150 mg/kg) 10 min before the imaging, then the animals were anaesthetized under isoflurane and imaged. Results are shown in FIGS. 8 and 9.

SEQUENCE LISTING (CD38 Homo sapiens; NP_001766.2)
SEQ ID NO: 1
MANCEFSPVSGDKPCCRLSRRAQLCLGVSILVLILVVVLAVVVPRWR
QQWSGPGTTKRFPETVLARCVKYTEIHPEMRHVDCQSVWDAFKGAFI
SKHPCNITEEDYQPLMKLGTQTVPCNKILLWSRIKDLAHQFTQVQRD
MFTLEDTLLGYLADDLTWCGEFNTSKINYQSCPDWRKDCSNNPVSVF
WKTVSRRFAEAACDVVHVMLNGSRSKIFDKNSTFGSVEVHNLQPEKV
QTLEAWVIHGGREDSRDLCQDPTIKELESIISKRNIQFSCKNIYRPD
KFLQCVKNPEDSSCTSEI (CD38 Macaca fascicularis; AAT36330.1)
SEQ ID NO: 2
MANCEFSPVSGDKPCCRLSRRAQVCLGVCLLVLLILVVVVAVVLPRW
RQQWSGSGTTSRFPETVLARCVKYTEVHPEMRHVDCQSVWDAFKGAF
ISKYPCNITEEDYQPLVKLGTQTVPCNKTLLWSRIKDLAHQFTQVQR
DMFTLEDMLLGYLADDLTWCGEFNTFEINYQSCPDWRKDCSNNPVSV
FWKTVSRRFAETACGVVHVMLNGSRSKIFDKNSTFGSVEVHNLQPEK
VQALEAWVIHGGREDSRDLCQDPTIKELESIISKRNIRFFCKNIYRP
DKFLQCVKNPEDSSCLSGI (HCDR1 Ab79)
SEQ ID NO: 3
GFTFDDYG (HCDR2 Ab79)
SEQ ID NO: 4
ISWNGGKT (HCDR3 Ab79)
SEQ ID NO: 5
ARGSLFHDSSGFYFGH (LCDR1 Ab79)
SEQ ID NO: 6
SSNIGDNY (LCDR2 Ab79)
SEQ ID NO: 7
RDS (LCDR3 Ab79)
SEQ ID NO: 8
QSYDSSLSGS (Heavy Chain Ab79)
SEQ ID NO: 9
EVQLLESGGGLVQPGGSLRLSCAASGFTFDDYGMSWVRQAPGKGLEW
VSDISWNGGKTHYVDSVKGQFTISRDNSKNTLYLQMNSLRAEDTAVY
YCARGSLFHDSSGFYFGHWGQGTLVTVSSASTKGPSVFPLA (Light Chain Ab79)
SEQ ID NO: 10
QSVLTQPPSASGTPGQRVTISCSGSSSNIGDNYVSWYQQLPGTAPKL
LIYRDSQRPSGVPDRFSGSKSGTSASLAISGLRSEDEADYYCQSYDS
SLSGSVFGGGTKLTVLGQPKANPTVTLFPPSSEEL (Heavy Chain Ab19)
SEQ ID NO: 11
EVQLLESGGGLVQPGGSLRLSCAASGFTFNNYDMTWVRQAPGKGLEW
VAVISYDGSDKDYADSVKGRFTISRDNSKNTLYLQMNSLRAEDTAVY
YCARVYYYGFSGPSMDVWGQGTLVTVSSASTKGPSVFPLA

SEQUENCE LISTING (Light Chain Ab19)
SEQ ID NO: 12
QSVLTQPPSASGTPGQRVTISCSGSNSNIGSNTVNWYQQLPGTAPKL
LIYSDSNRPSGVPDRFSGSKSGTSASLAISGLRSEDEADYYCQSYDS
SLSGSRVFGGGTKLTVLGQPKANPTVTLFPPSSEEL (HCDR1 Ab19)
SEQ ID NO: 13
GFTFNNYG (HCDR2 Ab19)
SEQ ID NO: 14
ISYDGSDK (HCDR3 Ab19)
SEQ ID NO: 15
ARVYYYGFSGPSMDV (LCDR1 Ab19)
SEQ ID NO: 16
NSNIGSNT (LCDR2 Ab19)
SEQ ID NO: 17
SDS (LCDR3 Ab79)
SEQ ID NO: 18
QSYDSSLSGSR (Heavy Chain Ab19) w/constant
SEQ ID NO: 19
EVQLLESGGGLVQPGGSLRLSCAASGFTFNNYDMTWVRQAPGKGLEW
VAVISYDGSDKDYADSVKGRFTISRDNSKNTLYLQMNSLRAEDTAVY
YCARVYYYGFSGPSMDVWGQGTLVTVSSASTKGPSVFPLAPSSKSTS
GGTAALGCLVKDYFPEPVTVSWNSGALTSGVHTFPAVLQSSGLYSLS
SVVTVPSSSLGTQTYICNVNHKPSNTKVDKRVEPKSCDKTHTCPPCP
APELLGGPSVFLFPPKPKDTLMISRTPEVTCVVVDVSHEDPEVKFNW
YVDGVEVHNAKTKPREEQYNSTYRVVSVLTVLHQDWLNGKEYKCKVS
NKALPAPIEKTISKAKGQPREPQVYTLPPSREEMTKNQVSLTCLVKG
FYPSDIAVEWESNGQPENNYKTTPPVLDSDGSFFLYSKLTVDKSRWQ
QGNVFSCSVMHEALHNHYTQKSLSLSPGK (Light Chain Ab19) w/constant
SEQ ID NO: 20
QSVLTQPPSASGTPGQRVTISCSGSNSNIGSNTVNWYQQLPGTAPKL
LIYSDSNRPSGVPDRFSGSKSGTSASLAISGLRSEDEADYYCQSYDS
SLSGSRVFGGGTKLTVLGQPKANPTVTLFPPSSEELQANKATLVCLI
SDFYPGAVTVAWKADGSPVKAGVETTKPSKQSNNKYAASSYLSLTPE
QWKSHRSYSCQVTHEGSTVEKTVAPTECS (Heavy Chain Ab79)
SEQ ID NO: 21
EVQLLESGGGLVQPGGSLRLSCAASGFTFDDYGMSWVRQAPGKGLEW
VSDISWNGGKTHYVDSVKGQFTISRDNSKNTLYLQMNSLRAEDTAVY
YCARGSLFHDSSGFYFGHWGQGTLVTVSSASTKGPSVFPLAPSSKST
SGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKV
SNKALPAPIEKTISKAKGQPREPQVYTLPPSREEMTKNQVSLTCLVK
GFYPSDIAVEWESNGQPENNYKTTPPVLDSDGSFFLYSKLTVDKSRW
QQGNVFSCSVMHEALHNHYTQKSLSLSPGK (Light Chain Ab79)
SEQ ID NO: 22
QSVLTQPPSASGTPGQRVTISCSGSSSNIGDNYVSWYQQLPGTAPKL
LIYRDSQRPSGVPDRFSGSKSGTSASLAISGLRSEDEADYYCQSYDS
SLSGSVFGGGTKLTVLGQPKANPTVTLFPPSSEELQANKATLVCLIS
DFYPGAVTVAWKADGSPVKAGVETTKPSKQSNNKYAASSYLSLTPEQ
WKSHRSYSCQVTHEGSTVEKTVAPTECS (CD157 Homo sapiens; NP_004325)
SEQ ID NO: 23
MAAQGCAASRLLQLLLQLLLLLLLAAGGARARWRGEGTSAHLRDIF
LGRCAEYRALLSPEQRNKNCTAIWEAFKVALDKDPCSVLPSDYDLFI
NLSRHSIPRDKSLFWENSHLLVNSFADNTRRFMPLSDVLYGRVADFL
SWCRQKNDSGLDYQSCPTSEDCENNPVDSFWKRASIQYSKDSSGVIH
VMLNGSEPTGAYPIKGFFADYEIPNLQKEKITRIEIWVMHEIGGPNV
ESCGEGSMKVLEKRLKDMGFQYSCINDYRPVKLLQCVDHSTHPDCAL
KSAAAATQRKAPSLYTEQRAGLIIPLFLVLASRTQL (Benchmark 1; Heavy Chain Variable Region)
SEQ ID NO: 24
EVQLLESGGGLVQPGGSLRLSCAVSGFTFNSFAMSWVRQAPGKGLEW
VSAISGSGGGTYYADSVKGRFTISRDNSKNTLYLQMNSLRAEDTAVY
FCAKDKILWFGEPVFDYWGQGTLVTVSS (Benchmark 1; Light Chain Variable Region)
SEQ ID NO: 25
EIVLTQSPATLSLSPGERATLSCRASQSVSSYLAWYQQKPGQAPRLL
IYDASNRATGIPARFSGSGSGTDFTLTISSLEPEDFAVYYCQQRSNW
PPTFGQGTKVEIKR (Benchmark 2; Heavy Chain Variable Region)
SEQ ID NO: 26
QVQLVQSGAEVAKPGTSVKLSCKASGYTFTDYWMQWVKQRPGQGLEW
IGTIYPGDGDTGYAQKFQGKATLTADKSSKTVYMHLSSLASEDSAVY
YCARGDYYGSNSLDYWGQGTSVTVSS (Benchmark 2; Light Chain Variable Region)
SEQ ID NO: 27
DIVMTQSHLSMSTLGDPVSITCKASQDVSTVVAWYQQKPGQSPRRLI
YSASYRYIGVPDRFTGSGAGTDFTFTISSVQAEDLAVYYCQQHYSPPY
TFGGGTKLEIKR (Heavy Chain Ab43)
SEQ ID NO: 28
EVQLLESGGGLVQPGGSLRLSCAASGFTFSSYGMHWVRQAPGKGLEWV
SRINSDGSSTSYADSMKGQFTISRDNSKNTLYLQMNSLRAEDTAVYYC
ARGGYYYYAMDVWGQGTLVTVSSASTKGPSVFPLAPSSKSTSGGTAAL
GCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHE
ALHNHYTQKSLSLSPGK (Light Chain Ab43)
SEQ ID NO: 29
QSVLTQPPSASGTPGQRVTISCSGGSSNIGYKTVNWYQQLPGTAPKL
IYDNNKRPSGVPDRFSGSKSGTSASLAISGLRSEDEADYYCAAWDDSL
NGLVFGGGTKLTVLGQPKANPTVTLFPPSSEELQANKATLVCLISDFY
PGAVTVAWKADGSPVKAGVETTKPSKQSNNKYAASSYLSLTPEQWKSH
RSYSCQVTHEGSTVEKTVAPTECS (Heavy Chain Ab72)
SEQ ID NO: 30
EVQLLESGGGLVQPGGSLRLSCAASGFTFSSYGMNWVRQAPGKGLEWV
SGISGSGGSTYYADSVKGRFTISRDNSKNTLYLQMNSLRAEDTAVYYC
AKDSNYDFWSGYYYGMDVWGQGTLVTVSSASTKGPSVFPLAPSSKSTS
GGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAP
ELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFS
CSVMHEALHNHYTQKSLSLSPGK (Light Chain Ab72)
SEQ ID NO: 31
QSVLTQPPSASGTPGQRVTISCSGSSSNIGSKTVSWYQQLPGTAPKLL
IYDNNKRPSGVPDRFSGSKSGTSASLAISGLRSEDEADYYCSSYAARS
TNIIFGGGTKLTVLGQPKANPTVTLFPPSSEELQANKATLVCLISDFY
PGAVTVAWKADGSPVKAGVETTKPSKQSNNKYAASSYLSLTPEQWKSH
RSYSCQVTHEGSTVEKTVAPTECS (Heavy Chain Ab110)
SEQ ID NO: 32
EVQLLESGGGLVQPGGSLRLSCAASGFTFSSYGMHWVRQAPGKGLEWV
SIIYSGGSTYYADSVKGRFTISRDNSKNTLYLQMNSLRAEDTAVYYCA
RRATWGGATHDYWGQGTLVTVSSASTKGPSVFPLAPSSKSTSGGTAAL
GCLVKDYFPEPVTVSWNSGALTSGVHTFPAVLQSSGLYSLSSVVTVPS

SEQUENCE LISTING

```
SSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHE
ALHNHYTQKSLSLSPGK (Light Chain Ab110)
                                          SEQ ID NO: 33
QSVLTQPPSASGTPGQRVTISCSGSSSNIGSNTVNWYQQLPGTAPKLL
IYRNNQRPSGVPDRFSGSKSGTSASLAISGLRSEDEADYYCATWDDSL
NGVLFGGGTKLTVLGQPKANPTVTLFPPSSEELQANKATLVCLISDFY
PGAVTVAWKADGSPVKAGVETTKPSKQSNNKYAASSYLSLTPEQWKSH
RSYSCQVTHEGSTVEKTVAPTECS (Heavy Chain Ab19) w/constant
                                          SEQ ID NO: 34
EVQLLESGGGLVQPGGSLRLSCAASGFTFNNYDMTWVRQAPGKGLEWV
AVISYDGSDKDYADSVKGRFTISRDNSKNTLYLQMNSLRAEDTAVYYC
ARVYYYGFSGPSMDVWGQGTLVTVSSASTKGPSVFPLAPSSKSTSGGT
AALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPELL
GGPSVFLFPPKPKDTLMISRTPEVTCVVVDVSHEDPEVKFNWYVDGVE
```

```
VHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSV
MHEALHNHYTQKSLSLSPGK (Light Chain Ab19) w/constant
                                          SEQ ID NO: 35
QSVLTQPPSASGTPGQRVTISCSGSNSNIGSNTVNWYQQLPGTAPKLL
IYSDSNRPSGVPDRFSGSKSGTSASLAISGLRSEDEADYYCQSYDSSL
SGSRVFGGGTKLTVLGQPKANPTVTLFPPSSEELQANKATLVCLISDF
YPGAVTVAWKADGSPVKAGVETTKPSKQSNNKYAASSYLSLTPEQWKS
HRSYSCQVTHEGSTVEKTVAPTECS
```

Having described the invention in detail and by reference to specific embodiments thereof, it will be apparent that modifications and variations are possible without departing from the scope of the invention defined in the appended claims. More specifically, although some aspects of the present invention are identified herein as particularily advantageous, it is contemplated that the present invention is not necessarily limited to these particular aspects of the invention.

We claim:

1. An isolated antibody which specifically binds human CD38 (SEQ ID NO:1) and cynomolgus CD38 (SEQ ID NO:2) comprising:
   a) a heavy chain variable region comprising:
      i) a first CDR comprising SEQ ID NO:3;
      ii) a second CDR comprising SEQ ID NO:4;
      iii) a third CDR comprising SEQ ID NO:5; and
   b) a light chain variable region comprising:
      i) a first CDR comprising SEQ ID NO:6;
      ii) a second CDR comprising SEQ ID NO:7;
      iii) a third CDR comprising SEQ ID NO:8; and
   c) a covalently attached drug moiety.

2. The isolated antibody according to claim 1 wherein said heavy chain variable region comprises SEQ ID NO:9 and said light chain variable region comprises SEQ ID NO:10.

3. The isolated antibody according to claim 1 wherein the heavy chain comprises SEQ ID NO:21 and the light chain comprises SEQ ID NO:22.

4. An isolated antibody which specifically binds human CD38 (SEQ ID NO:1) and cynomolgus CD38 (SEQ ID NO:2) comprising:
   a) a heavy chain variable region comprising:
      i) a first CDR comprising SEQ ID NO:13;
      ii) a second CDR comprising SEQ ID NO:14;
      iii) a third CDR comprising SEQ ID NO:15; and
   b) a light chain variable region comprising:
      i) a first CDR comprising SEQ ID NO:16;
      ii) a second CDR comprising SEQ ID NO:17;
      iii) a third CDR comprising SEQ ID NO:18; and
   c) a covalently attached drug moiety.

5. The isolated antibody according to claim 4 wherein said heavy chain variable region comprises SEQ ID NO:19 and said light chain variable region comprises SEQ ID NO:20.

6. The isolated antibody according to claim 4 wherein the heavy chain comprises SEQ ID NO:34 and the light chain comprises SEQ ID NO:35.

7. The isolated antibody according to claim 1 further comprising an Fc domain.

8. The isolated antibody according to claim 7 wherein said Fc domain is human.

9. The isolated antibody according to claim 7 wherein said Fc domain is a variant Fc domain.

10. The isolated antibody according to claim 1 wherein said drug moiety is attached to said antibody using a linker.

11. The isolated antibody according to claim 10 wherein said drug moiety is selected from the group consisting of an auristatin, a maytansinoid, and calicheamicin, a dolstatin, and a trichothecene.

12. An isolated nucleic acid encoding the heavy chain of claim 1.

13. An isolated nucleic acid encoding the light chain of claim 1.

14. A host cell comprising the isolated nucleic acids of claim 12.

15. A method of producing the antibody of claim 1 comprising culturing a host cell comprising the isolated nucleic acid encoding the heavy chain of claim 1 under conditions wherein said antibody is produced.

16. A method of inhibiting the biological activity of human CD38 protein (SEQ ID NO: 1) and cynomolgus CD38 (SEQ ID NO:2) by contacting said protein with an antibody that interacts with at least K121, F135, Q139, D141, E239, W241, C275, K276, F284, P291 and E292 of SEQ ID NO:1 and SEQ ID NO:2.

17. A method of treating a cancer expressing CD38 comprising administering to a patient in need thereof an isolated antibody which specifically binds human CD38 (SEQ ID NO:1) and cynomolgus CD38 (SEQ ID NO:2) comprising:
   a) a heavy chain variable region comprising:
      i) a first CDR comprising SEQ ID NO:3;
      ii) a second CDR comprising SEQ ID NO:4;
      iii) a third CDR comprising SEQ ID NO:5; and
   b) a light chain variable region comprising:
      i) a first CDR comprising SEQ ID NO:6;
      ii) a second CDR comprising SEQ ID NO:7;
      iii) a third CDR comprising SEQ ID NO:8; and
   c) a covalently attached drug moiety.

* * * * *

SEQUENCE LISTING

```
<160> NUMBER OF SEQ ID NOS: 35

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205
```

```
Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 301
<212> TYPE: PRT
<213> ORGANISM: Macaca fascicularis

<400> SEQUENCE: 2

Met Ala Asn Cys Glu Phe Ser Pro Val Ser Gly Asp Lys Pro Cys Cys
1               5                   10                  15

Arg Leu Ser Arg Arg Ala Gln Val Cys Leu Gly Val Cys Leu Leu Val
            20                  25                  30

Leu Leu Ile Leu Val Val Val Ala Val Val Leu Pro Arg Trp Arg
        35                  40                  45

Gln Gln Trp Ser Gly Ser Gly Thr Thr Ser Arg Phe Pro Glu Thr Val
50                  55                  60

Leu Ala Arg Cys Val Lys Tyr Thr Glu Val His Pro Glu Met Arg His
65                  70                  75                  80

Val Asp Cys Gln Ser Val Trp Asp Ala Phe Lys Gly Ala Phe Ile Ser
                85                  90                  95

Lys Tyr Pro Cys Asn Ile Thr Glu Glu Asp Tyr Gln Pro Leu Val Lys
            100                 105                 110

Leu Gly Thr Gln Thr Val Pro Cys Asn Lys Thr Leu Leu Trp Ser Arg
        115                 120                 125

Ile Lys Asp Leu Ala His Gln Phe Thr Gln Val Gln Arg Asp Met Phe
130                 135                 140

Thr Leu Glu Asp Met Leu Leu Gly Tyr Leu Ala Asp Asp Leu Thr Trp
145                 150                 155                 160

Cys Gly Glu Phe Asn Thr Phe Glu Ile Asn Tyr Gln Ser Cys Pro Asp
                165                 170                 175

Trp Arg Lys Asp Cys Ser Asn Asn Pro Val Ser Val Phe Trp Lys Thr
            180                 185                 190

Val Ser Arg Arg Phe Ala Glu Thr Ala Cys Gly Val Val His Val Met
        195                 200                 205

Leu Asn Gly Ser Arg Ser Lys Ile Phe Asp Lys Asn Ser Thr Phe Gly
    210                 215                 220

Ser Val Glu Val His Asn Leu Gln Pro Glu Lys Val Gln Ala Leu Glu
225                 230                 235                 240

Ala Trp Val Ile His Gly Gly Arg Glu Asp Ser Arg Asp Leu Cys Gln
                245                 250                 255

Asp Pro Thr Ile Lys Glu Leu Glu Ser Ile Ile Ser Lys Arg Asn Ile
            260                 265                 270
```

```
Arg Phe Phe Cys Lys Asn Ile Tyr Arg Pro Asp Lys Phe Leu Gln Cys
            275                 280                 285

Val Lys Asn Pro Glu Asp Ser Ser Cys Leu Ser Gly Ile
    290                 295                 300

<210> SEQ ID NO 3
<211> LENGTH: 8
<212> TYPE: PRT
<213> ORGANISM: Artificial Sequence
<220> FEATURE:
<223> OTHER INFORMATION: Ab79 Heavy Chain CDR1

<400> SEQUENCE: 3

Gly Phe Thr Phe Asp Asp Tyr Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Ab79 Heavy Chain CDR2

<400> SEQUENCE: 4

Ile Ser Trp Asn Gly Gly Lys Thr
1               5

<210> SEQ ID NO 5
<211> LENGTH: 16
<212> TYPE: PRT
<213> ORGANISM: Artificial Sequence
<220> FEATURE:
<223> OTHER INFORMATION: Ab79 Heavy Chain CDR3

<400> SEQUENCE: 5

Ala Arg Gly Ser Leu Phe His Asp Ser Ser Gly Phe Tyr Phe Gly His
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: Ab79 Light Chain CDR1

<400> SEQUENCE: 6

Ser Ser Asn Ile Gly Asp Asn Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: Ab79 Light Chain CDR2

<400> SEQUENCE: 7

Arg Asp Ser
1

<210> SEQ ID NO 8
<211> LENGTH: 10
<212> TYPE: PRT
<213> ORGANISM: Artificial Sequence
<220> FEATURE:
<223> OTHER INFORMATION: Ab79 Light Chain CDR3
```

```
<400> SEQUENCE: 8

Gln Ser Tyr Asp Ser Ser Leu Ser Gly Ser
1               5                   10

<210> SEQ ID NO 9
<211> LENGTH: 135
<212> TYPE: PRT
<213> ORGANISM: Artificial Sequence
<220> FEATURE:
<223> OTHER INFORMATION: Ab79 Heavy Chain Variable Region

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Asp Ile Ser Trp Asn Gly Gly Lys Thr His Tyr Val Asp Ser Val
    50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Phe His Asp Ser Ser Gly Phe Tyr Phe Gly His
            100                 105                 110

Trp Gly Gln Gly Thr Leu Val Thr Val Ser Ser Ala Ser Thr Lys Gly
        115                 120                 125

Pro Ser Val Phe Pro Leu Ala
        130                 135

<210> SEQ ID NO 10
<211> LENGTH: 129
<212> TYPE: PRT
<213> ORGANISM: Artificial Sequence
<220> FEATURE:
<223> OTHER INFORMATION: Ab79 Light Chain Variable Region

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asp Asn
            20                  25                  30

Tyr Val Ser Trp Tyr Gln Gln Leu Pro Gly Thr Ala Pro Lys Leu Leu
        35                  40                  45

Ile Tyr Arg Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu
```

<210> SEQ ID NO 11
<211> LENGTH: 134
<212> TYPE: PRT
<213> ORGANISM: Artificial Sequence
<220> FEATURE:
<223> OTHER INFORMATION: Ab19 Heavy Chain

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Asp Met Thr Trp Val Arg Gln Ala Pro Gly Lys Gly Leu Glu Trp Val
        35                  40                  45

Ala Val Ile Ser Tyr Asp Gly Ser Asp Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Tyr Gly Phe Ser Gly Pro Ser Met Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala
    130

<210> SEQ ID NO 12
<211> LENGTH: 130
<212> TYPE: PRT
<213> ORGANISM: Artificial Sequence
<220> FEATURE:
<223> OTHER INFORMATION: Ab19 Light Chain

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Arg Val Phe Gly Gly Gly Thr Lys Leu Thr Val Leu Gly
            100                 105                 110

Gln Pro Lys Ala Asn Pro Thr Val Thr Leu Phe Pro Pro Ser Ser Glu
        115                 120                 125

Glu Leu
    130

<210> SEQ ID NO 13
<211> LENGTH: 8
<212> TYPE: PRT
<213> ORGANISM: Artificial Sequence

```
<220> FEATURE:
<223> OTHER INFORMATION: Ab19 Heavy Chain CDR1

<400> SEQUENCE: 13

Gly Phe Thr Phe Asn Asn Tyr Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Ab19 Heavy Chain CDR2

<400> SEQUENCE: 14

Ile Ser Tyr Asp Gly Ser Asp Lys
1               5

<210> SEQ ID NO 15
<211> LENGTH: 15
<212> TYPE: PRT
<213> ORGANISM: Artificial Sequence
<220> FEATURE:
<223> OTHER INFORMATION: Ab19 Heavy Chain CDR3

<400> SEQUENCE: 15

Ala Arg Val Tyr Tyr Tyr Gly Phe Ser Gly Pro Ser Met Asp Val
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Ab19 Light Chain CDR1

<400> SEQUENCE: 16

Asn Ser Asn Ile Gly Ser Asn Thr
1               5

<210> SEQ ID NO 17
<211> LENGTH: 3
<212> TYPE: PRT
<213> ORGANISM: Artificial Sequence
<220> FEATURE:
<223> OTHER INFORMATION: Ab19 Light Chain CDR2

<400> SEQUENCE: 17

Ser Asp Ser
1

<210> SEQ ID NO 18
<211> LENGTH: 11
<212> TYPE: PRT
<213> ORGANISM: Artificial Sequence
<220> FEATURE:
<223> OTHER INFORMATION: Ab19 Light Chain CDR3

<400> SEQUENCE: 18

Gln Ser Tyr Asp Ser Ser Leu Ser Gly Ser Arg
1               5                   10

<210> SEQ ID NO 19
<211> LENGTH: 452
<212> TYPE: PRT
<213> ORGANISM: Artificial Sequence
```

```
<220> FEATURE:
<223> OTHER INFORMATION: Ab19 Heavy Chain

<400> SEQUENCE: 19

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
            20                  25                  30

Asp Met Thr Trp Val Arg Gln Ala Pro Gly Lys Gly Leu Glu Trp Val
        35                  40                  45

Ala Val Ile Ser Tyr Asp Gly Ser Asp Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Gly Phe Ser Gly Pro Ser Met Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 20
<211> LENGTH: 217
<212> TYPE: PRT
<213> ORGANISM: Artificial Sequence
<220> FEATURE:
<223> OTHER INFORMATION: Ab19 Light Chain

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asp Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Arg Val Phe Gly Gly Gly Thr Lys Leu Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 21
<211> LENGTH: 453
<212> TYPE: PRT
<213> ORGANISM: Artificial Sequence
<220> FEATURE:
<223> OTHER INFORMATION: Ab79 Heavy Chain

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30
```

```
Gly Met Ser Trp Val Arg Gln Ala Pro Gly Lys Gly Leu Glu Trp Val
            35                  40                  45

Ser Asp Ile Ser Trp Asn Gly Gly Lys Thr His Tyr Val Asp Ser Val
 50                  55                  60

Lys Gly Gln Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Ser Leu Phe His Asp Ser Ser Gly Phe Tyr Phe Gly His
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
            435                 440                 445

Leu Ser Pro Gly Lys
    450

<210> SEQ ID NO 22
<211> LENGTH: 216
<212> TYPE: PRT
<213> ORGANISM: Artificial Sequence
<220> FEATURE:
<223> OTHER INFORMATION: Ab79 Light Chain

<400> SEQUENCE: 22

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asp Asn
            20                  25                  30

Tyr Val Ser Trp Tyr Gln Gln Leu Pro Gly Thr Ala Pro Lys Leu Leu
            35                  40                  45

Ile Tyr Arg Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 23
<211> LENGTH: 318
<212> TYPE: PRT
<213> ORGANISM: Homo sapiens

<400> SEQUENCE: 23

Met Ala Ala Gln Gly Cys Ala Ala Ser Arg Leu Leu Gln Leu Leu Leu
1               5                   10                  15

Gln Leu Leu Leu Leu Leu Leu Leu Ala Ala Gly Gly Ala Arg Ala
            20                  25                  30

Arg Trp Arg Gly Glu Gly Thr Ser Ala His Leu Arg Asp Ile Phe Leu
            35                  40                  45

Gly Arg Cys Ala Glu Tyr Arg Ala Leu Leu Ser Pro Glu Gln Arg Asn
    50                  55                  60

Lys Asn Cys Thr Ala Ile Trp Glu Ala Phe Lys Val Ala Leu Asp Lys
65                  70                  75                  80

Asp Pro Cys Ser Val Leu Pro Ser Asp Tyr Asp Leu Phe Ile Asn Leu
                85                  90                  95

Ser Arg His Ser Ile Pro Arg Asp Lys Ser Leu Phe Trp Glu Asn Ser
            100                 105                 110

His Leu Leu Val Asn Ser Phe Ala Asp Asn Thr Arg Arg Phe Met Pro
        115                 120                 125

Leu Ser Asp Val Leu Tyr Gly Arg Val Ala Asp Phe Leu Ser Trp Cys
130                 135                 140

Arg Gln Lys Asn Asp Ser Gly Leu Asp Tyr Gln Ser Cys Pro Thr Ser
145                 150                 155                 160

Glu Asp Cys Glu Asn Asn Pro Val Asp Ser Phe Trp Lys Arg Ala Ser
                165                 170                 175

Ile Gln Tyr Ser Lys Asp Ser Ser Gly Val Ile His Val Met Leu Asn
            180                 185                 190

Gly Ser Glu Pro Thr Gly Ala Tyr Pro Ile Lys Gly Phe Phe Ala Asp
        195                 200                 205

Tyr Glu Ile Pro Asn Leu Gln Lys Glu Lys Ile Thr Arg Ile Glu Ile
210                 215                 220

Trp Val Met His Glu Ile Gly Gly Pro Asn Val Glu Ser Cys Gly Glu
225                 230                 235                 240

Gly Ser Met Lys Val Leu Glu Lys Arg Leu Lys Asp Met Gly Phe Gln
                245                 250                 255

Tyr Ser Cys Ile Asn Asp Tyr Arg Pro Val Lys Leu Leu Gln Cys Val
            260                 265                 270

Asp His Ser Thr His Pro Asp Cys Ala Leu Lys Ser Ala Ala Ala Ala
        275                 280                 285

Thr Gln Arg Lys Ala Pro Ser Leu Tyr Thr Glu Gln Arg Ala Gly Leu
290                 295                 300

Ile Ile Pro Leu Phe Leu Val Leu Ala Ser Arg Thr Gln Leu
305                 310                 315

<210> SEQ ID NO 24
<211> LENGTH: 122
<212> TYPE: PRT
<213> ORGANISM: Artificial Sequence
<220> FEATURE:
<223> OTHER INFORMATION: Benchmark 1 Heavy Chain

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 25
<211> LENGTH: 108
<212> TYPE: PRT
<213> ORGANISM: Artificial Sequence
<220> FEATURE:
<223> OTHER INFORMATION: Benchmark 1 Light Chain

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg
            100                 105

<210> SEQ ID NO 26
<211> LENGTH: 120
<212> TYPE: PRT
<213> ORGANISM: Artificial Sequence
<220> FEATURE:
<223> OTHER INFORMATION: Benchmark 2 Heavy Chain

<400> SEQUENCE: 26

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 27
<211> LENGTH: 108
<212> TYPE: PRT
<213> ORGANISM: Artificial Sequence
<220> FEATURE:
<223> OTHER INFORMATION: Benchmark 2 Light Chain

<400> SEQUENCE: 27

```
Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105
```

<210> SEQ ID NO 28
<211> LENGTH: 449
<212> TYPE: PRT
<213> ORGANISM: Artificial Sequence
<220> FEATURE:
<223> OTHER INFORMATION: Ab43 Heavy Chain

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Arg Ile Asn Ser Asp Gly Ser Ser Thr Ser Tyr Ala Asp Ser Met
    50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Tyr Tyr Ala Met Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 29
<211> LENGTH: 216
<212> TYPE: PRT
<213> ORGANISM: Artificial Sequence
<220> FEATURE:
<223> OTHER INFORMATION: Ab43 Light Chain

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Tyr Lys
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Leu Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 30
<211> LENGTH: 455
<212> TYPE: PRT
<213> ORGANISM: Artificial Sequence
<220> FEATURE:
<223> OTHER INFORMATION: Ab72 Heavy Chain

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Ser Asn Tyr Asp Phe Trp Ser Gly Tyr Tyr Tyr Gly Met
            100                 105                 110

Asp Val Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
450                 455

<210> SEQ ID NO 31
<211> LENGTH: 216
<212> TYPE: PRT
<213> ORGANISM: Artificial Sequence
<220> FEATURE:
<223> OTHER INFORMATION: Ab72 Light Chain

<400> SEQUENCE: 31

Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Lys
            20                  25                  30
Thr Val Ser Trp Tyr Gln Gln Leu Pro Gly Thr Ala Pro Lys Leu Leu
        35                  40                  45
Ile Tyr Asp Asn Asn Lys Arg Pro Ser Gly Val Pro Asp Arg Phe Ser
50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ser Ser Tyr Ala Ala Arg Ser
                85                  90                  95
Thr Asn Ile Ile Phe Gly Gly Gly Thr Lys Leu Thr Val Leu Gly Gln
            100                 105                 110
Pro Lys Ala Asn Pro Thr Val Thr Leu Phe Pro Pro Ser Ser Glu Glu
        115                 120                 125
Leu Gln Ala Asn Lys Ala Thr Leu Val Cys Leu Ile Ser Asp Phe Tyr
130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190

-continued

```
Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 32
<211> LENGTH: 449
<212> TYPE: PRT
<213> ORGANISM: Artificial Sequence
<220> FEATURE:
<223> OTHER INFORMATION: Ab110 Heavy Chain

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ile Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Arg Ala Thr Trp Gly Gly Ala Thr His Asp Tyr Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 33
<211> LENGTH: 216
<212> TYPE: PRT
<213> ORGANISM: Artificial Sequence
<220> FEATURE:
<223> OTHER INFORMATION: Ab110 Light Chain

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Asn Gly Val Leu Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 34
<211> LENGTH: 452
<212> TYPE: PRT
<213> ORGANISM: Artificial Sequence
<220> FEATURE:
<223> OTHER INFORMATION: Ab119 Heavy Chain

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Asp Met Thr Trp Val Arg Gln Ala Pro Gly Lys Gly Leu Glu Trp Val
        35                  40                  45

Ala Val Ile Ser Tyr Asp Gly Ser Asp Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Tyr Gly Phe Ser Gly Pro Ser Met Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
        450
```

<210> SEQ ID NO 35
<211> LENGTH: 217
<212> TYPE: PRT
<213> ORGANISM: Artificial Sequence
<220> FEATURE:
<223> OTHER INFORMATION: Ab19 Light Chain

<400> SEQUENCE: 35

```
Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Arg Val Phe Gly Gly Gly Thr Lys Leu Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```